(12) United States Patent
Mowris et al.

(10) Patent No.: US 12,038,204 B2
(45) Date of Patent: *Jul. 16, 2024

(54) IONIZER FEEDBACK CONTROL

(71) Applicants: Robert J. Mowris, Olympic Valley, CA (US); James Lau, Tustin, CA (US)

(72) Inventors: Robert J. Mowris, Olympic Valley, CA (US); John Walsh, Bozeman, MT (US); James Lau, Tustin, CA (US)

( * ) Notice: Subject to any disclaimer, the term of this patent is extended or adjusted under 35 U.S.C. 154(b) by 93 days.

This patent is subject to a terminal disclaimer.

(21) Appl. No.: 18/100,399

(22) Filed: Jan. 23, 2023

(65) Prior Publication Data
US 2023/0160586 A1    May 25, 2023

Related U.S. Application Data

(63) Continuation-in-part of application No. 17/527,115, filed on Nov. 15, 2021, now Pat. No. 11,563,310, (Continued)

(51) Int. Cl.
*H01T 23/00* (2006.01)
*A61L 9/22* (2006.01)
(Continued)

(52) U.S. Cl.
CPC ............... *F24F 8/194* (2021.01); *A61L 9/22* (2013.01); *F24F 11/32* (2018.01); *F24F 11/50* (2018.01);
(Continued)

(58) Field of Classification Search
None
See application file for complete search history.

(56) References Cited

U.S. PATENT DOCUMENTS 4,729,057 A    3/1988  Halleck
5,055,963 A   10/1991  Partridge
(Continued)

OTHER PUBLICATIONS

Yicheng Zeng, et al., Evaluating a commercially available in-duct bipolar ionization device for pollutant removal and potential by product formation, Building and Environment Journal, May 15, 2021, 14 pages, vol. 195. Elsevier Science Direct. Building and Environment. Amsterdam, Netherlands. https://www.sciencedirect.com/science/article/pii/S036013232100158X.
(Continued)

*Primary Examiner* — Stephen W Jackson
(74) *Attorney, Agent, or Firm* — CIONCA IP Law P.C.

(57) ABSTRACT

The ionizer feedback control converts high-voltage signals to feedback signals to monitor the corresponding high-voltage signals and compares the feedback signals to a first specification to determine whether the feedback signals are within the first specification. The ionizer varies a frequency and a duty cycle of a digital signal to control an excitation signal for a step-up transformer and modulates the frequency and the duty cycle of a step-up transformer output voltage to consistently maintain the feedback signals within the first specification and maintain the high-voltage signals within a second specification to generate consistent ion concentrations over a range of electrical signal inputs. The microprocessor calculates and reports high-voltage signals, and ion concentrations based on feedback signals. The microprocessor monitors concentrations of Volatile Organic Compounds (VOCs) in an airflow serving the ionizer and adjusts the high-voltage signals and ion concentration when VOC concentrations are above a threshold.

22 Claims, 18 Drawing Sheets

Related U.S. Application Data which is a continuation-in-part of application No. 17/244,389, filed on Apr. 29, 2021, now Pat. No. 11,173,226.

(51) Int. Cl.
*F24F 8/192* (2021.01)
*F24F 11/32* (2018.01)
*F24F 11/50* (2018.01)
*F24F 11/63* (2018.01)
*F24F 110/66* (2018.01)

(52) U.S. Cl.
CPC .............. *F24F 11/63* (2018.01); *H01T 23/00* (2013.01); *A61L 2209/111* (2013.01); *A61L 2209/12* (2013.01); *A61L 2209/14* (2013.01); *A61L 2209/16* (2013.01); *F24F 2110/66* (2018.01)

(56) References Cited

U.S. PATENT DOCUMENTS

| | | | |
|---|---|---|---|
| 6,118,645 A | 9/2000 | Partridge | |
| 6,504,702 B1* | 1/2003 | Noll | H01T 23/00 361/220 |
| 6,515,458 B1 | 2/2003 | Partridge | |
| 6,693,788 B1 | 2/2004 | Partridge | |
| 7,120,006 B2 | 10/2006 | Sekoguchi | |
| 7,177,133 B2 | 2/2007 | Riskin | |
| 7,254,006 B2 | 8/2007 | Sekoguchi | |
| 7,256,979 B2 | 8/2007 | Sekoguchi | |
| 7,312,973 B2 | 12/2007 | Sekoguchi | |
| 7,961,451 B2 | 6/2011 | Sekoguchi | |
| 8,009,405 B2 | 8/2011 | Gefter | |
| 8,106,367 B2 | 1/2012 | Riskin | |
| 8,576,535 B2 | 11/2013 | Sekoguchi | |
| 8,611,065 B2 | 12/2013 | Riskin | |
| 8,624,476 B2 | 1/2014 | Sekoguchi | |
| 8,710,456 B2 | 4/2014 | Klochkov | |
| 8,773,837 B2 | 7/2014 | Partridge | |
| 8,773,838 B2 | 7/2014 | Takeda | |
| 8,861,167 B2 | 10/2014 | Waddell | |
| 9,142,378 B2 | 9/2015 | Sekoguchi | |
| 9,421,291 B2 | 8/2016 | Robert | |
| 9,510,431 B2 | 11/2016 | Oldynski | |
| 9,843,169 B2 | 12/2017 | Riskin | |
| 9,918,374 B2 | 3/2018 | Oldynski | |
| 9,922,792 B2 | 3/2018 | Nishida | |
| 9,985,420 B2 | 5/2018 | Sekoguchi | |
| 10,073,055 B2 | 9/2018 | Waddell | |
| 10,109,449 B2 | 10/2018 | Ezaki | |
| 10,128,075 B2 | 11/2018 | Waddell | |
| 10,317,096 B2 | 6/2019 | Waddell | |
| 10,319,569 B2 | 6/2019 | Waddell | |
| 10,322,205 B2 | 6/2019 | Waddell | |
| 10,383,970 B2 | 8/2019 | Waddell | |
| 10,566,769 B2 | 2/2020 | Waddell | |
| 10,695,455 B2 | 6/2020 | Waddell | |
| 10,710,123 B2 | 7/2020 | Waddell | |
| 10,737,279 B2 | 8/2020 | Gefter | |
| 10,786,818 B2 | 9/2020 | Galbreath | |
| 10,910,186 B2 | 2/2021 | Nishida | |
| 11,173,226 B1* | 11/2021 | Mowris | A61L 9/22 |
| 11,563,310 B2* | 1/2023 | Walsh | H01T 23/00 |
| 2007/0103842 A1 | 5/2007 | Partridge | |
| 2010/0014635 A1 | 2/2010 | Vaynerman | |
| 2015/0059580 A1 | 3/2015 | Clement | |
| 2016/0167059 A1 | 6/2016 | Waddell | |
| 2016/0367712 A1 | 12/2016 | Robert | |
| 2019/0247893 A1 | 8/2019 | Waddell | |
| 2020/0161839 A1 | 5/2020 | Waddell | |
| 2020/0179557 A1 | 6/2020 | Waddell | |
| 2020/0340679 A1 | 10/2020 | Waddell | |
| 2020/0388994 A1 | 12/2020 | Waddell | |

OTHER PUBLICATIONS

M. Sidheswaren, H. Detaillats, D. Sullivan, J. Larsen, W. Fisk, Quantitative Room Temperature Mineralization of Airborne Formaldehyde Using Manganese Oxide Catalysts, Jun. 2011, pp. 29, LBNL-5169E, Lawrence Berkeley National Laboratory, Berkeley, CA USA. https://indoor.lbl.gov/sites/all/files/lbnl-5169e.pdf.

T. Licht, T. Schutze. Power Cycling Induced Failure Mechanisms in High Temperature Applications, May/Jun. 2008, 3 pages. Issue 4, 2008. Power Electronics Europe. Tonbridge, Great Britain. http://www.power-mag.com/pdf/feature_pdf/1222954864_PEE_Issue_4_2008_Power_Module_Reliability-Power_Cycling_Induced_Failure_Mechanisms_in_High_Temperature_Applications.pdf.

* cited by examiner

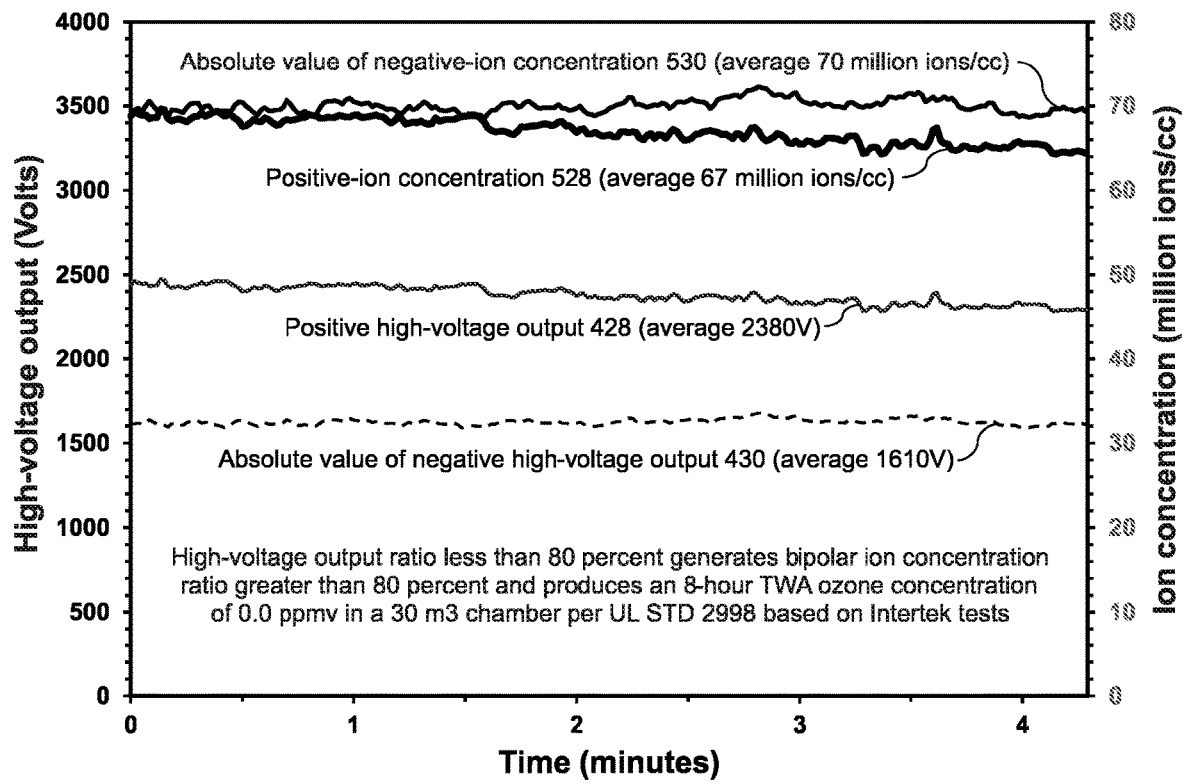

FIG. 8

| | | High-voltage output ratio < 80% and bipolar ion concentration ratio > 80% | | | | | | |
|---|---|---|---|---|---|---|---|---|
| # | Input voltage VAC | Positive high-voltage output (VDC) | Absolute value of negative high-voltage output (VDC) | High-voltage output ratio | Positive-ion concentration (million ions/cc) | Absolute value of negative-ion concentration (million ions/cc) | Bipolar ion concentration ratio | Ozone (ppm) |
| 1 | 20 | 1970 | 1320 | 67% | 54 | 63 | 86% | 0.0 |
| 2 | 24 | 2380 | 1610 | 68% | 67 | 70 | 96% | 0.0 |
| 3 | 29.3 | 2970 | 2020 | 68% | 72 | 78 | 92% | 0.0 |
| 4 | 20 | 1430 | 2150 | 67% | 53 | 63 | 84% | 0.0 |
| 5 | 24 | 1720 | 2530 | 68% | 65 | 76 | 86% | 0.0 |
| 6 | 29.2 | 2050 | 3180 | 64% | 70 | 83 | 84% | 0.0 |

FIG. 9

| Known prior art high-voltage output ≥ 90% and bipolar ion concentration ratio ≤ 80% | | | | | | | |
|---|---|---|---|---|---|---|---|
| # | Input voltage VAC | Positive high-voltage output (VDC) | Absolute value of negative high-voltage output (VDC) | High-voltage output ratio | Positive-ion concentration (million ions/cc) | Absolute value of negative-ion concentration (million ions/cc) | Bipolar ion concentration ratio | Ozone (ppm) |
| 7 | 20 | 1407 | 1408 | 100% | 59 | 39 | 66% | 0.08 |
| 8 | 24 | 1413 | 1431 | 99% | 65 | 46 | 71% | 0.12 |
| 9 | 29.3 | 1433 | 1600 | 90% | 71 | 55 | 77% | 0.27 |

FIG. 10

IONIZER FEEDBACK CONTROL

CROSS-REFERENCE TO RELATED APPLICATIONS

The present application is a Continuation In Part of U.S. patent application Ser. No. 17/527,115 filed on Nov. 15, 2021, and U.S. patent application Ser. No. 17/244,389 filed on Apr. 29, 2021 and issued as U.S. Pat. No. 11,173,226 issued on Nov. 16, 2021, which applications are incorporated by reference in their entirely.

TECHNICAL FIELD

This invention relates generally to the field of air treatment, and more particularly to apparatus and methods for an ionizer. Examples include applications to improve indoor air quality in buildings, automobiles, airplanes, trains, boats, transportation systems, refrigeration systems, or enclosed environments with Heating, Ventilating, Air Conditioning (HVAC) systems.

BACKGROUND OF THE INVENTION

Known ionizers are generally installed at an inlet of a fan installed on a Heating, Ventilating, Air Conditioning (HVAC) system. Ionizers may also be installed on a fan motor or a fan blade or inside an air duct or on the inlet of a fan of an air cleaner. Known ionizers are used to produce high concentrations of positive and/or negative ions which attach to particles in a volume of air or particles in an airflow volume causing said particles to become positively and/or negatively charged and combine with other particles which become larger and heavier. Clusters of larger and heavier particles are removed from the air by air filters or removed from the air by being attracted to surfaces in a duct system or surfaces inside a building. Ions are also attracted to virus, bacteria, mold, and other airborne pathogenic microbes. When ions combine on the surface of a pathogen, a chemical reaction occurs on the cell surface membrane which produces hydroxide (OH+ or OH−) radicals which removes a hydrogen atom (H) from the pathogen. This chemical reaction severs a protein on the cell membrane which deactivates or destroys the pathogen. The ionized OH radicals bond with the removed hydrogen and form water vapor (H2O). Ionization kills pathogens without damaging the DNA in the interior cells of the pathogen, so it does not cause cancer. Ionization may partially or fully break down Volatile Organic Compound (VOC) hydrocarbon chains into harmless compounds such as oxygen, nitrogen, water vapor, and carbon dioxide. Ionization also removes dust and odors.

The California Air Resources Board (CARB) adopted a regulation to limit ozone emissions from indoor air cleaning devices (AB 2276). Since 2010, all indoor air cleaners sold in, or shipped to, California must meet ozone emission and electrical safety standards and produce a Time Weighted Average (TWA) ozone concentration less than 0.050 parts per million by volume (ppmv) over 8 hours when tested in a 30 meter cubed (m3) chamber. https://ww2.arb.ca.gov/sites/default/files/2017-08/acrfactsheet.pdf https://ww2.arb.ca.gov/sites/default/files/2020-03/air-cleaner-regulation.pdf https://ww2.arb.ca.gov/resources/fact-sheets/californias-regulation-limit-ozone-emissions-indoor-air-cleaning-devices. The United States (US) Food and Drug Administration (FDA) requires ozone output of indoor medical devices to be no more than 0.05 ppmv. See https://www.accessdata.fda.gov/scripts/cdrh/cfdocs/cfcfr/CFRSearch.cfm?fr=801.415. The US Occupational Safety and Health Administration (OSHA) requires that workers not be exposed to an average concentration of more than 0.10 ppmv for 8 hours. The US Environmental Protection Agency (EPA) ozone standard is a maximum 8 hour average concentration of 0.08 ppmv. See https://www.epa.gov/indoor-air-quality-iaq/ozone-generators-are-sold-air-cleaners#ozone-health.

Known ionizers may operate over a range of electrical signal inputs from 20 Volts Alternating Current (VAC) to 30 VAC or line voltages from 120 to 277 VAC. Ionizers for HVAC systems are typically designed to operate at 24 VAC, but HVAC system transformer voltages may vary from 24 to 30 VAC. Known ionizers operating at transformer voltages from 24 to 30 VAC may provide higher ozone concentrations than allowed by the CARB and US FDA. The Underwriters Laboratories (UL) 867 Section 40 ozone concentration tests or the Canadian Standards Association (CSA) 22.2 Number 187 in-duct ozone concentration tests are used to certify polar and bipolar ionizers for public safety. These tests might provide false positive results if tests are only performed at a single transformer voltage of 24 VAC.

Field tests indicate that some ionizers are sensitive to magnetic fields from rare earth magnets used to attach bipolar ionizers to sheet metal surfaces of HVAC ducts or fan housings. An ionizer with two rare earth magnets installed by the Original Equipment Manufacturer (OEM) caused ion concentrations to be reduced from 50 to 100 million ions per cubic centimeter (ions/cc) to 50 to 100 ions/cc. Lower ion concentration reduces the efficacy of ionizers to remove particles, break down VOCs, and inactivate airborne pathogens.

Known prior art ionizers only have one electrical signal input (and a common signal input) which typically requires the ionizer to be energized continuously which will cause dust to accumulate on the electrodes when the fan is turned off. Dust accumulation may require maintenance. Operating a fan continuously to power the ionizer continuously will significantly increase the fan energy use.

According to the National Institute of Standards and Technology (NIST) gas phase ion energetics data, the ozone gas ionization energy is 12.53±0.08 electron Volts (eV). See https://webbook.nist.gov/cgi/cbook.cgi?ID=C10028156&Mask=20#Ion-Energetics. The threshold high-voltage output is dependent on and may vary based on an ambient air temperature and a relative humidity as well as a distance the positive-ion electrode is from a grounded surface and the distance the positive-ion electrode is from the negative-ion electrode.

A 2021 research study by YICHENG ZENG indicates that bipolar ionizers may not fully decompose Volatile Organic Compounds (VOCs). See YICHENG ZENG, et al., Evaluating a commercially available in-duct bipolar ionization device for pollutant removal and potential by product formation, Building and Environment Journal, May 15, 2021, 14 pages, Volume 195. Elsevier Science Direct. Building and Environment. Amsterdam, NL. https://www.sciencedirect.com/science/article/pii/S036013232100158X ZENG page 12 states that both "the laboratory and field data collected herein suggest that other unintended byproduct formation (e.g., of smaller, potentially oxidized VOCs) is likely occurring, with some consistencies observed in both constituent reductions (e.g., xylene, ethylbenzene, and 1,2-dichloroethane) and increases (e.g., acetone, ethanol, and toluene), with some consistencies observed between both the chamber tests and field tests." ZENG page 12 further indicates that "if the residence time in the ionizing region is insufficient to fully ionize not only the parent VOCs initially in the indoor air, but also the multiple generations of daughter products, then the unintended consequence of ionizers may be to enhance concentrations of smaller, potentially oxidized daughter VOCs."

There are thousands of VOCs, and some VOCs such as formaldehyde, have been recognized as a health risk and have specific guidelines. The United States (US) Occupational Safety and Health Administration (OSHA) regulates formaldehyde as a carcinogen. OSHA has adopted an 8-hour Time Weighted Average (TWA) Permissible Exposure Limit (PEL) for formaldehyde of 0.75 ppmv and an action level of 0.5 ppmv. According to the OSHA Standard Number 1910.1048(n)(1) for formaldehyde, employers shall not expose employees to formaldehyde at or above 0.1 ppmv. The US Department of Housing and Urban Development (HUD) has established an ambient level for formaldehyde of 0.4 ppmv or less for mobile homes.

Based on the OSHA 8-hour TWA PEL of 0.75 ppmv and action level of 0.5 ppmv and employee exposure limit of 0.1 ppmv for formaldehyde, the HUD formaldehyde level of 0.4 ppmv for mobile homes, and research findings published by ZENG regarding "unintended consequence of ionizers may be to enhance concentrations of smaller, potentially oxidized daughter VOCs," an unresolved problem exists regarding bipolar ionizers operating in an airflow where VOCs such as formaldehyde may be present at concentration levels at or above 0.1 ppmv.

A 2011 report by SIDHESWARAN, titled "Quantitative Room Temperature Mineralization of Airborne Formaldehyde Using Manganese Oxide Catalysts," indicated that air filters with manganese oxide catalysts (manganese sulfate or MnSO4 and sodium permanganate or NaMnO4) showed consistent single-pass formaldehyde oxidation efficiency greater than 80% for the synthesized catalysts, which remained active over at least 35 days. Catalysts were prepared by co-precipitation of MnSO4 and NaMnO4 followed by curing at 100, 200 and 400 C. Characterization was performed using X-ray diffractometry (XRD), porosimetry, scanning electron microscopy (SEM), and Inductively Coupled Plasma-Mass Spectrometry (ICP-MS). Diffractograms of samples treated at 100 and 200 C matched those of nsutite and cryptomelane (K(Mn4+,Mn2+)8O16) or manjiroite (Na(Mn4+7Mn3+)O16) structures, with high BET surface area (up to 149 m2/g) and small particle size (<50 nm), while curing at 400 C yielded pyrolusite with lower effective surface area. The BET or Brunauer, Emmett and Teller theory is used to evaluate gas adsorption expressed in units of area per mass sample (m2/g). Room temperature catalytic oxidation of airborne formaldehyde was studied by supporting the catalyst on a particulate filter media placed in a flow system, under stable upstream formaldehyde concentrations between 30 and 200 parts per billion (ppb). Two different face velocities (v=0.2 and 50 cm/s) were studied to evaluate the oxidation efficiency under different flow regimes using formaldehyde-enriched laboratory air at 25-30% relative humidity. Results showed consistent single-pass formaldehyde oxidation efficiency greater than 80% for the synthesized catalysts, which remained active over at least 35 days of continuous operation at v=0.2 cm/s and were able to process up to 400 m3 of air at v=50 cm/s without appreciable deactivation. Operation under high relative humidity (>90% RH) produced only a small reversible reduction in formaldehyde removal. Most significantly, 100% mineralization yields were verified by quantifying CO2 formation downstream of the catalyst for upstream formaldehyde concentrations as high as 6 ppm and a face velocity of v=13 cm/s. See M. SIDHESWAREN, H. DETAILLATS, D. SULLIVAN, J. LARSEN, W. FISK, Quantitative Room Temperature Mineralization of Airborne Formaldehyde Using Manganese Oxide Catalysts, June 2011, Pages 29, LBNL-5169E, Lawrence Berkeley National Laboratory, Berkeley, CA USA. https://indoor.lbl.gov/sites/all/files/IbnI-5169e.pdf.

BRIEF SUMMARY OF THE INVENTION

The present invention ionizer provides solutions to the unresolved problems of deactivating pathogens such as the SARS-CoV-2 virus while not producing ozone, and the unintended consequences of enhancing concentrations of smaller, potentially oxidized daughter Volatile Organic Compounds (VOCs) such as formaldehyde (HCHO). Specifically, the present invention comprises a feedback control to provide a consistent Direct Current (DC) high-voltage electrode output over a range of 20 to 30 Volts Alternating Current (VAC) electric signal inputs to provide a consistent negative ion concentration or a consistent bipolar ion concentration to deactivate pathogens and produce zero ozone concentrations. The present invention also comprises a feedback control to provide an unbalanced DC high-voltage output ratio less than 80 percent over a range of 20 to 30 VAC electric signal inputs to provide a balanced bipolar ion concentration ratio greater than 80 percent to deactivate pathogens and produce zero ozone concentrations. The present invention also comprises sensors to monitor VOCs and/or HCHO in the airflow being treated by the ionizer. If the monitored VOC and/or HCHO concentrations are greater than an eight-hour (8-hour) Time Weighted Average (TWA) Permissible Exposure Limit (PEL) for formaldehyde of 0.75 ppmv and an action level of 0.5 parts per million by volume (ppmv) or greater than 0.1 to 0.4 ppmv for VOCs, then the present invention de-energizes or reduces a positive DC high-voltage output and/or a negative DC high-voltage output to stop generating the ion concentration or reduce the ion concentration to avoid producing or enhancing concentrations of smaller, potentially oxidized daughter VOCs or HCHO. The VOC or HCHO sensors may be mounted up or downstream of the bipolar ionizer. An air filter may also be mounted upstream of the ionizer to remove VOCs, HCHO, and PM 2.25. The air filter may comprise at least one air filter selected from the group consisting of: a Minimum Efficiency Reporting Value (MERV) rated air filter with activated carbon, a High Efficiency Particulate Air (HEPA) filter, or the MERV rated air filter with manganese oxide catalysts such as a manganese sulfate or MnSO4 catalyst, a sodium permanganate or NaMnO4 catalyst, and a cryptomelane potassium manganese oxide mineral or K(Mn4+, Mn2+)8O16 catalyst. The air filter may comprise manganese oxide catalysts to remove formaldehyde through catalytic oxidation to the avoid producing concentrations of smaller, potentially oxidized daughter VOCs such as HCHO.

The unbalanced DC high-voltage output ratio is equal to a minimum of an absolute value of a negative DC high-voltage output and a positive DC high-voltage output divided by a maximum of the absolute value of the negative DC high-voltage output and the positive DC high-voltage output. The bipolar ion concentration ratio is equal to a minimum of an absolute value of a negative-ion concentration and a positive-ion concentration divided by a maximum of the absolute value of the negative-ion concentration and the positive-ion concentration.

Based on tests performed by Intertek, an ISO-certified independent laboratory, the present invention bipolar ionizer provides a 24-hour TWA ozone concentration of 0.0 ppmv in a 30 meter cubed (m3) chamber per Underwriters Laboratories (UL) Standard (STD) 867 (Electrostatic Air Cleaners) and UL STD 2998 Environmental Claim Validation Procedure (ECVP) for Zero Ozone Emissions from Air Cleaners. Zero ozone is significantly less than the California Air Resources Board (CARB) and United States (US) Food and Drug Administration (FDA) ozone exposure limit of 0.05 ppmv for 8 to 24 hours.

Some known prior art bipolar ionizers provide ozone concentrations greater than the CARB ozone exposure limit of 0.05 ppmv for 8 to 24 hours due to providing DC high-voltage output ratios greater than or equal to 80 percent and bipolar ion concentration ratios less than or equal to 80 percent. The present invention provides a solution to this unresolved problem by providing feedback control to maintain a consistent unbalanced DC high-voltage less than 80 percent at the positive and negative electrodes and balanced bipolar ion concentrations greater than 80 percent to produce zero ozone concentrations which are significantly less than the CARB and US FDA ozone exposure limit of 0.050 ppmv across a range of transformer voltages from 20 to 30 VAC and line voltages from 120 to 480 VAC.

Based on tests performed by Innovative Bioanalysis, the present invention bipolar ionizer deactivates 97.6 percent of an aerosolized sample of the SARS-CoV-2 delta variant virus within 60 minutes where the aerosolized virus sample is introduced into a chamber 20 feet long by 8 feet wide by 8 feet high with the bipolar ionizer installed at the inlet of a fan circulating air in the chamber similar to a typical Heating, Ventilating, Air Conditioning (HVAC) system fan. Innovative Bioanalysis is an independent Class 3 laboratory (College of American Pathologists (CAP) License 8860298, Clinical Laboratory Improvement Amendments (CLIA) License 05D0955926, California State ID CLF 00324630). The present invention may also be installed downstream of an air filter on a fan inlet or a fan outlet of an air purifier, an automobile HVAC system (12 VDC), a box fan, or an air circulation system inside a refrigerator.

The present invention comprises an apparatus and/or methods to monitor the positive and/or negative DC high-voltage signals on the positive and/or negative electrodes and process at least one feedback signal and calculate and report an ion concentration based on the at least one feedback signal. Apparatus and/or methods are disclosed to monitor concentrations of VOCs and/or HCHO in the airflow being treated by the ionizer. If the monitored VOC and/or HCHO concentrations are greater than a threshold, for example 0.1 to 0.4 ppm, then the present invention de-energizes or adjusts a positive and/or a negative DC high-voltage output to stop generating the ion concentration or adjust the ion concentration to avoid producing potentially multiple generations of daughter products or enhancing concentrations of smaller, potentially oxidized daughter VOCs or HCHO. When the VOC or HCHO concentration drops below the threshold, the method may energize or adjust the positive and/or the negative DC high-voltage output to enable the ionizer to continue generating an ion concentration to treat the air and deactivate pathogens such as viruses, molds, or fungi.

The present invention may also provide "soft power cycling" comprising rebooting a microprocessor controlling the ionizer for several minutes or a short period of time (e.g., 1 to 10 minutes) after a fan providing airflow to the ionizer has been operating continuously for more than several hours or a specified time period (e.g., 1 to 10 hours). Soft power cycling will enhance an ionizer lifetime (e.g., an electronic circuit or a microprocessor) and clear accumulated errors in the microprocessor (if present). Soft power cycling avoids hard power cycling which can stress hardware and lead to failures due to repeated inrush currents. The method also turns off the ionizer when the fan is not operating consistent with UL 867 which requires fan operation with ionizer operation.

The present invention may provide a method to send data and/or messages to a software application on a computer, a mobile phone, a watch, or other electronic communications technology regarding the DC high-voltage output and ion concentration, the VOC concentration, or the HCHO concentration. The data and/or alarm messages may be sent to a user using at least one communication method selected from the group consisting of: a graphical display, a text message, an email message, an audio communication message, or a wireless communication message. The wireless communication may use a cellular system, a WIFI (wireless fidelity), a Bluetooth (short-range wireless using UHF radio waves in the ISM bands, from 2.402 GHz to 2.480 GHz), a Low-Power Wide-Area Network (LPWAN with data rates from 0.3 kbit/s to 50 kbit/s per channel), or an ultra-low power Long-range Radio (LoRa) or LoRA Wide Area Network (LoRaWAN) communication protocol.

The ionizer comprises a signal conditioning element to process an electrical signal input and provide an excitation signal to a step-up transformer which provides an output voltage to positive and/or negative voltage multipliers which provide a positive high-voltage output greater than an absolute value of a negative high-voltage output or vice versa to a positive-ion electrode and/or a negative-ion electrode. The range of electrical signal inputs may be selected from the group consisting of: 20 to 30 Volts Alternating Current (VAC), 110 to 130 VAC, 210 to 250 VAC, 208 to 280 VAC, 2 to 15 Volts Direct Current (VDC), and 20 to 30 VDC. The signal conditioning element may comprise at least one: wire, opto-isolator, diode, Zener diode, resistor, capacitor, a microprocessor (or oscillator "OSC"), Field Effect Transistor (FET), input and/or output feedback circuit, Resistor Divider Network (RDN), operational amplifier (Op Amp), or comparator. The positive and negative voltage multipliers generate a DC high-impedance high-voltage output to the positive or negative electrodes. The positive or negative multipliers are comprised of one or more voltage multiplier stages where each voltage multiplier stage is comprised of two capacitors and two diodes (e.g., "Cockroft-Walton" multiplier). The Positive Voltage Multiplier (PVM) may provide at least one more multiplier stage than the Negative Voltage Multiplier (NVM) or vice versa. One embodiment provides +2.5+/−0.6 kilo-Volts (kV) on the positive and −1.7 kV+/−0.4 kV on the negative-ion electrode or +1.7 kV+/−0.4 kV on the positive and −2.5+/−0.6 kV on the negative-ion electrode.

Another embodiment of the ionizer comprises an input voltage feedback circuit and a microprocessor that monitors a step-up transformer DC input voltage and continuously adjusts a frequency and duty cycle of a digital signal to the FET to produce an excitation signal for the step-up transformer to produce an output voltage to the positive and negative voltage multipliers to create the positive and negative high-voltage outputs to the positive and negative-ion electrodes. A duty cycle is a fraction of a period when a signal is active (e.g., 0 to 100 percent). A period is the time it takes for a signal to complete one on-off cycle. The frequency varies from 8 to 12 kiloHertz (kHz) where kHz is a unit of alternating current or electromagnetic (EM) wave frequency equal to one thousand Hertz (1,000 Hz).

Another embodiment may include a high-voltage output feedback circuit, an active element, and a microprocessor to continuously adjust the frequency and duty cycle of the digital signal to the FET to produce the excitation signal for the step-up transformer to achieve the positive and negative high-voltage outputs to the positive and negative-ion electrodes.

The ionizer is not impacted by the position or polarity of rare earth magnets fastened to the surface of the bipolar ionizer to attach the bipolar ionizer to sheet metal used for the Heating, Ventilating, Air Conditioning (HVAC) duct work or blower fan housings. Another embodiment provides status or fault alarm information using a Light Emitting Diode (LED) or wireless communication. Another embodiment of the balanced bipolar ionizer may include at least one electrical signal input to energize the ionizer by more than one control signal to allow ionizer operation during a thermostat call for cooling or heating without operating a thermostat Fan G signal continuously. This embodiment will save HVAC energy.

BRIEF DESCRIPTION OF THE SEVERAL VIEWS OF THE DRAWINGS

The above and other aspects, features and advantages of the ionizer will be more apparent from the following more particular description thereof, presented in conjunction with the following drawings.

FIG. 8 shows time series measurements of high-voltage output and the sampled bipolar ion concentration versus time for the ionizer.

FIG. 9 provides test results for the ionizer with high-voltage output less than 80 percent with produces zero or very low ozone concentrations.

FIG. 10 provides test results for a known prior art bipolar ionizer with high-voltage output greater than or equal to 90% which produces high ozone concentrations.

Corresponding reference characters indicate corresponding elements throughout the several views of the drawings.

DETAILED DESCRIPTION OF THE INVENTION

The following description is the best mode presently contemplated of an ionizer with feedback control to provide consistent Direct Current (DC) high-voltage output and consistent ion concentrations to minimize ozone concentration to zero parts per million by volume (ppmv) over a range of input voltages. This description is not to be taken in a limiting sense, but is made merely for the purpose of describing one or more preferred embodiments of the invention. The scope of the invention should be determined with reference to the claims.

Figure 1:
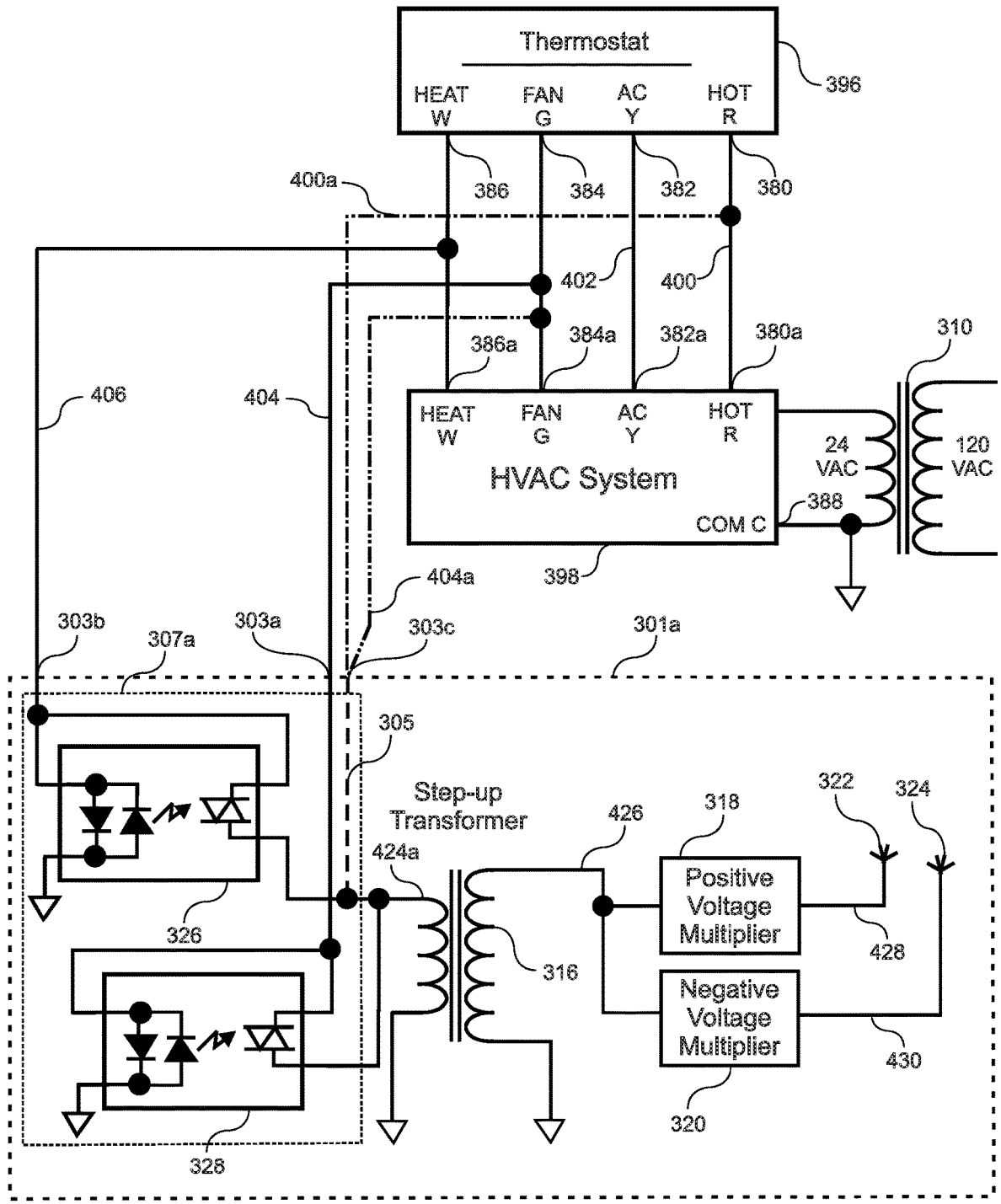
FIG. 1 shows a first embodiment of the ionizer with a step-up transformer, positive and/or negative voltage multipliers, and a first signal conditioning element using a first wire for a first electrical signal input to a first opto-isolator and a second wire for a second electrical signal input to a second opto-isolator.

FIG. 1 shows a first embodiment of the ionizer 301a (large dashed line) with a first signal conditioning element 307a (small dashed line), a step-up transformer 316, a Positive Voltage Multiplier 318 (PVM) connected to a positive-ion electrode 322, and a Negative Voltage Multiplier 320 (NVM) connected to a negative-ion electrode 324. The first signal conditioning element 307a comprises: 1) a first input terminal 303a connected to a first opto-isolator 328 connected to the step-up transformer 316, 2) a second input terminal 303b connected to a second opto-isolator 326 connected to the step-up transformer 316, and 3) an alternative third input terminal 303c connected to a wire 305 connected to the step-up transformer 316. The alternative third input terminal 303c is only used for a single input embodiment shown receiving a second fan G signal 404a (dash-dot-dot-dash line) or a second hot R signal 400a (dash-dot-dash line).

FIG. 1 shows a fan G signal 404 connected to the first input terminal 303a and a heat W signal 406 connected to the second input terminal 303b. The opto-isolators allow either the first electrical signal input or the second electrical signal input (e.g., fan G signal 404, heat W signal 406) to energize the ionizer 301a without causing a short circuit if both signals are energized simultaneously. A low-voltage alternating current signal on any of the signal input terminals will produce an excitation signal 424a to the step-up transformer 316 to generate a step-up transformer output voltage 426. FIG. 1 shows the electrical connections from a thermostat 396 to a Heating, Ventilation, Air Conditioning (HVAC) system (HVAC system 398), and a 120 Volts Alternating Current (VAC) to a low-voltage 24 VAC transformer (hereafter referred to as a 24 VAC transformer 310). The transformer may comprise other electrical signal input voltages. The thermostat 396 may include a hot R terminal 380, an Air Conditioning (AC) Y terminal (AC Y terminal 382), a fan G terminal 384, a heat W terminal 386, and a COM C terminal (not shown) typically connected to the COM C terminal 388 of the HVAC system 398 (shown as a ground). The HVAC system 398 may include a hot R terminal 380a, an AC Y terminal 382a, a fan G terminal 384a, a heat W terminal 386a, and a COM C terminal 388. A hot R signal 400 is shown as a solid line from the hot R terminal 380 of the thermostat 396 to the hot R terminal 380a of the HVAC system 398, and the hot R terminal 380a of the HVAC system 398 is connected to the hot R terminal of the 24 VAC transformer 310. An AC Y signal 402 is shown as a solid line from the AC Y terminal 382 to the AC Y terminal 382a of the HVAC system 398.

FIG. 1 shows the step-up transformer output voltage 426 from the step-up transformer 316 is conducted to a positive voltage multiplier 318 and a negative voltage multiplier 320. The positive voltage multiplier generates a DC high-impedance Positive High-voltage Output (PHO 428) on a positive-ion electrode 322. The negative voltage multiplier generates a DC high-impedance Negative High-voltage Output (NHO 430) on a negative-ion electrode 324. The positive voltage multiplier 318 and the negative voltage multiplier 320 contain an unequal number of multiplier stages to produce a high-voltage output ratio less than 80 percent and a bipolar ion concentration ratio greater than 80 percent. The high-voltage output ratio is equal to a minimum of an absolute value of a negative high-voltage output and a positive high-voltage output, divided by a maximum of the absolute value of the negative high-voltage output and the positive high-voltage output. The bipolar ion concentration ratio is equal to a minimum of an absolute value of a negative-ion concentration and a positive-ion concentration, divided by a maximum of the absolute value of the negative-ion concentration and the positive-ion concentration. High-voltage Output Ratio (HOR) is calculated using Equation 1.

$$HOR=[MIN(ABS(NHO),PHO)]/[MAX(ABS(NHO),PHO)]$$ Eq. 1

Where, HOR=High-voltage Output Ratio (fraction),
MIN=Minimum value,
ABS=absolute value,
MAX=Maximum value,
PHO=Positive High-voltage Output or PHO 428 (DC Volts), and
NHO=Negative High-voltage Output or NHO 430 (DC Volts).

Figure 2:
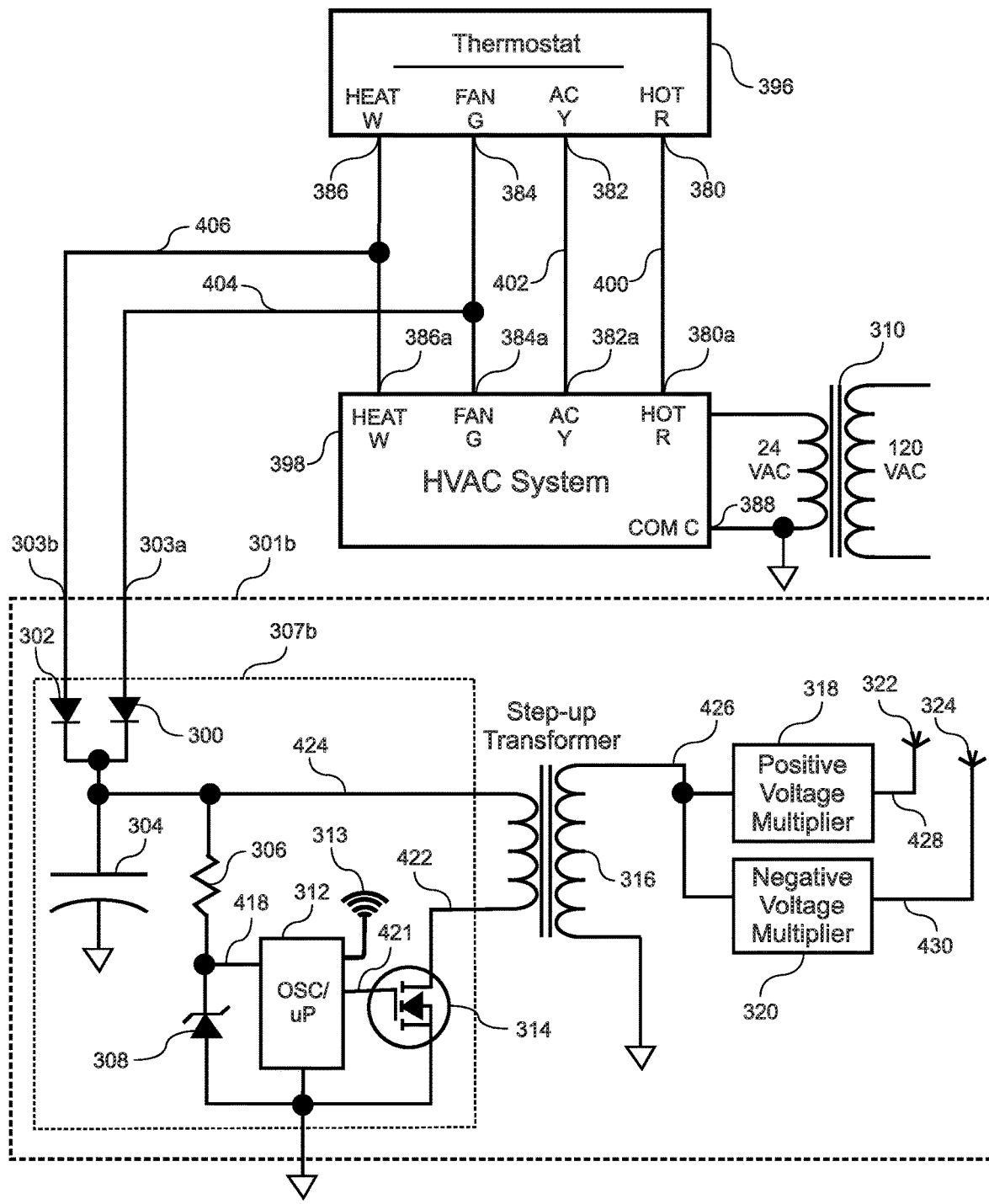
FIG. 2 shows a second embodiment with two input terminals, two diodes, a capacitor, a resistor, a Zener diode, a microprocessor or oscillator, and a Field Effect Transistor (FET).

FIG. 2 shows a second embodiment of the ionizer 301b with a second signal conditioning element 307b, the step-up transformer 316, the positive voltage multiplier 318 connected to the positive-ion electrode 322, and the negative voltage multiplier 320 connected to the negative-ion electrode 324. The thermostat 396 and the HVAC system 398 have the same terminals and electrical signals shown in FIG. 1. The second signal conditioning element 307b comprises: 1) a first input terminal 303a and a second input terminal 303b, 2) signal input processing circuit (a first diode 300, a second diode 302, a first capacitor 304, a first resistor 306, a first Zener diode 308), 3) a microprocessor (or an oscillator "OSC"), and a first Field Effect Transistor (FET) (first FET 314). If the oscillator is used, then the oscillator may include at least one resistor and at least one capacitor. The first diode 300 and the second diode 302 rectify low-voltage 24 VAC signals from the thermostat or 24 VAC transformer and pass a positively rectified signal to the first capacitor 304 which creates the step-up transformer DC input voltage 424 to the step-up transformer 316. The first resistor 306 limits the current from the step-up transformer DC input voltage 424 that feeds the first Zener diode 308 to create a +5 Volt signal 418 to the microprocessor 312. The +5 Volt signal 418 may be created using other components or methods.

FIG. 2 shows the microprocessor 312 drives the gate of the first FET 314 with a digital signal 421 which may be a 0 Volt signal or a +5 Volt signal that varies in frequency and duty cycle to create the excitation signal 422 to the step-up transformer 316. When the first FET 314 is driven with a positive digital signal, the first FET 314 is energized and draws current from the step-up transformer DC input voltage 424 through the step-up transformer 316 to create a magnetic field within the core of the step-up transformer 316. When the first FET 314 is driven with a zero digital signal, the first FET 314 is gated off and the magnetic field in the step-up transformer 316 collapses which generates the step-up transformer output voltage 426. The step-up transformer output voltage 426 is passed to the positive voltage multiplier 318 and the negative voltage multiplier 320 which contain an unequal number of multiplier stages to produce a high-voltage output ratio less than 80 percent and a bipolar ion concentration ratio greater than 80 percent.

Figure 3:
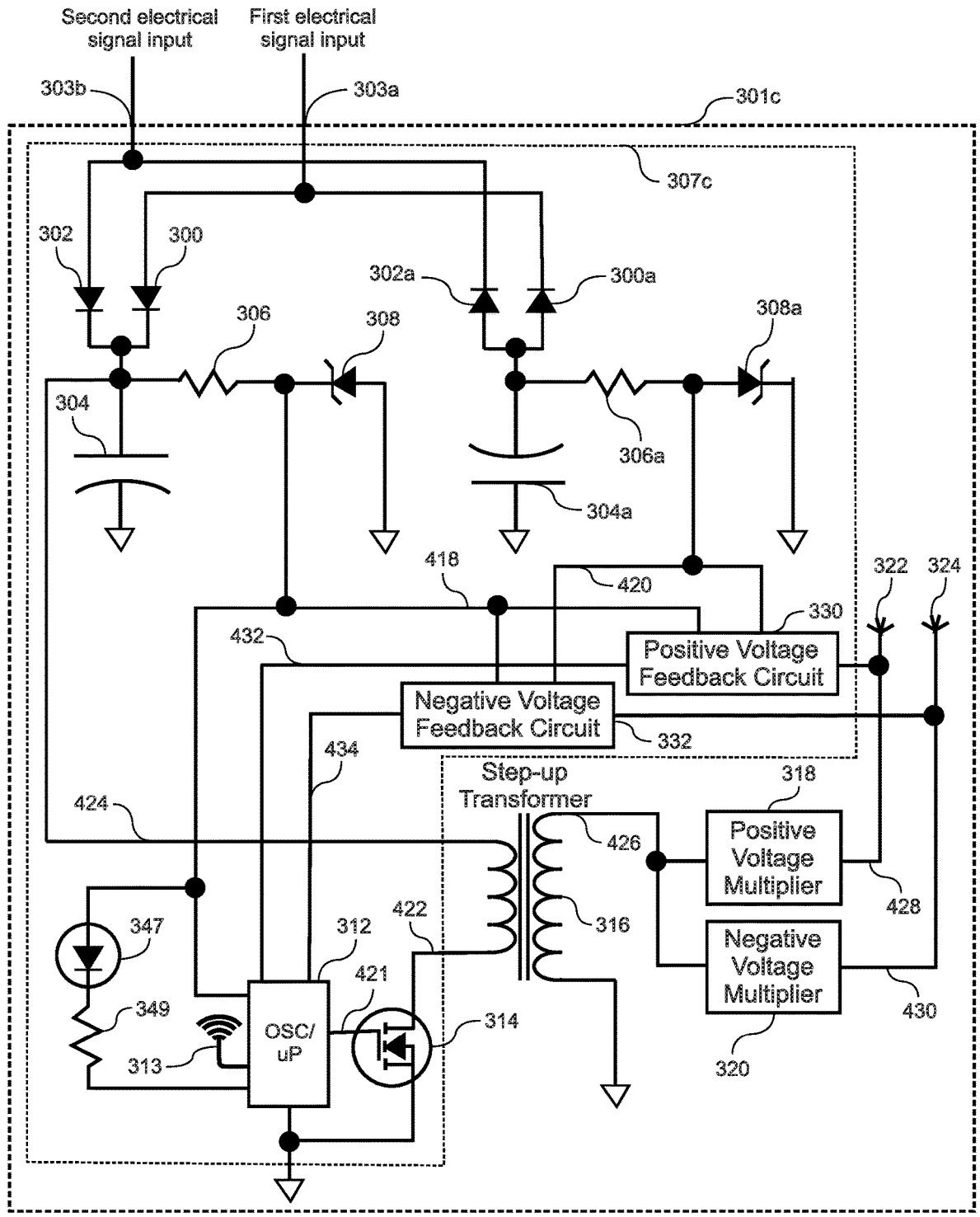
FIG. 3 shows a third embodiment of the ionizer with a third signal conditioning element with a positive and a negative feedback circuit.

FIG. 3 shows a third embodiment of the ionizer 301c with a third signal conditioning element 307c, the step-up transformer 316, the positive voltage multiplier 318 connected to the positive-ion electrode 322, and the negative voltage multiplier 320 connected to the negative-ion electrode 324. The third signal conditioning element 307c comprises: 1) a first input terminal 303a and a second input terminal 303b, 2) signal input processing circuit (a first diode 300, a second diode 302, a first capacitor 304, a first resistor 306, a first Zener diode 308, a third diode 300a, a fourth diode 302a, a second capacitor 304a, a second resistor 306a, a second Zener diode 308a), 3) a microprocessor 312 that provides a digital signal 421 to a first FET 314 which provides an excitation signal 422 to the step-up transformer 316, and 4) a positive voltage feedback circuit 330 and a negative voltage feedback circuit 332. Also shown is a wireless antenna 313 to provide information regarding the status of the balanced bipolar ionizer. The wireless communication may use a cellular system, a WIFI (wireless fidelity) network, a Bluetooth network (short-range wireless using UHF radio waves in the ISM bands, from 2.402 GHz to 2.480 GHz), a Low-Power Wide-Area Network (LPWAN with data rates from 0.3 kbit/s to 50 kbit/s per channel), or an ultra-low power Long-range Radio (LoRa) or LoRA Wide Area Network (LoRaWAN) communication protocol. The positive and negative voltage feedback circuits allow the microprocessor 312 to modulate the frequency and duty cycle of the step-up transformer output voltage 426 to consistently maintain at least one DC high-voltage signal on a negative-ion electrode or a positive-ion electrode to generate a consistent negative or positive ion concentration over a range of electrical signal inputs selected from the group consisting of: 20 to 30 Volts Alternating Current (VAC), 110 to 130 VAC, 210 to 250 VAC, 208 to 280 VAC, 2 to 15 Volts Direct Current (VDC), and 20 to 30 VDC.

FIG. 3 shows a first input terminal 303a connected to a first diode 300 and a third diode 300a and a second input terminal 303b connected to a second diode 302, and a fourth diode 302a. The first diode 300 is used to rectify a first electrical signal input (e.g., the fan G signal 404, the heat W signal 406, or the hot R signal), and pass the positively rectified signals to the first capacitor 304 which creates a DC voltage used as the step-up transformer DC input voltage 424. The first resistor 306 limits the current from the step-up transformer DC input voltage 424 to the first Zener diode 308 to create a +5 Volt signal 418 to the microprocessor 312. The +5 volts signal 418 is also used by the positive voltage feedback circuit 330 and the negative voltage feedback circuit 332. The third diode 300a and the fourth diode 302a negatively rectify the first electrical signal input and the second electrical signal input and pass the negatively rectified signals to the second capacitor 304a which creates a negative DC voltage. The second resistor 306a limits the current from the second capacitor 304a to the second Zener diode 308a to create a −5 Volt signal 420 used by the positive voltage feedback circuit 330 and the negative voltage feedback circuit 332.

FIG. 3 shows the positive voltage feedback circuit 330 and the negative voltage feedback circuit 332 which contain at least one Resistor Divider Network (RDN) and one active element (not shown) to reduce the PHO 428 and NHO 430 to a Positive Low-voltage Feedback Signal (PLFS 432) and Negative Low-voltage Feedback Signal (NLFS 434). The positive voltage feedback circuit 330 and the negative voltage feedback circuit 332 reduce and convert at least one DC high-voltage signal to at least one feedback signal where the at least one DC high-voltage signal is selected from the group consisting of: a Negative DC High-voltage Signal (NDHS) or NHO 430 on a negative-ion electrode 324 used to generate a negative-ion concentration 530, and a Positive DC High-voltage Signal (PDHS) or PHO 428 on a positive-ion electrode 322 used to generate a positive-ion concentration 528. The at least one feedback signal is selected from the group consisting of: the NLFS 434, and the PLFS 432.

The microprocessor 312 monitors the at least one feedback signal corresponding to the at least one DC high-voltage signal and compares the at least one feedback signal to a first specification to determine whether the at least one feedback signal is within a first specification. The at least one feedback signal is used by the microprocessor 312 to vary a frequency and a duty cycle of a digital signal 421 to a first FET 314 to control an excitation signal 422 for a step-up transformer 316 and modulate the frequency and the duty cycle of a step-up transformer output voltage 426 to consistently maintain the at least one DC high-voltage signal output (NDHS or NHO 430 and PDHS or PHO 428) within a second specification to generate a consistent ion concentration over a range of electrical signal inputs.

Figure 6:
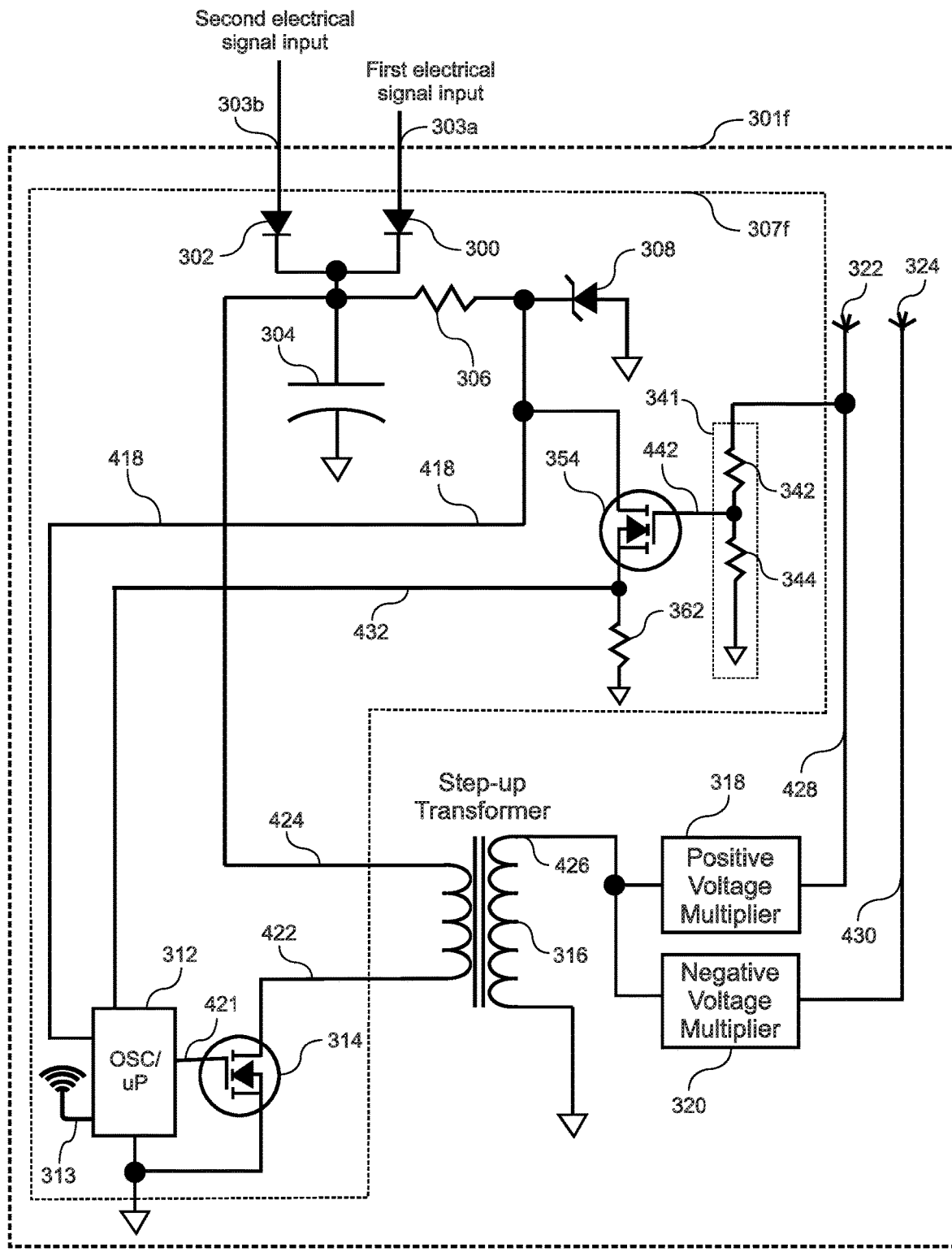
FIG. 6 shows a sixth embodiment of the ionizer with a feedback circuit based on a Field Effect Transistor (FET) attached to the high-voltage output.
Figure 7:
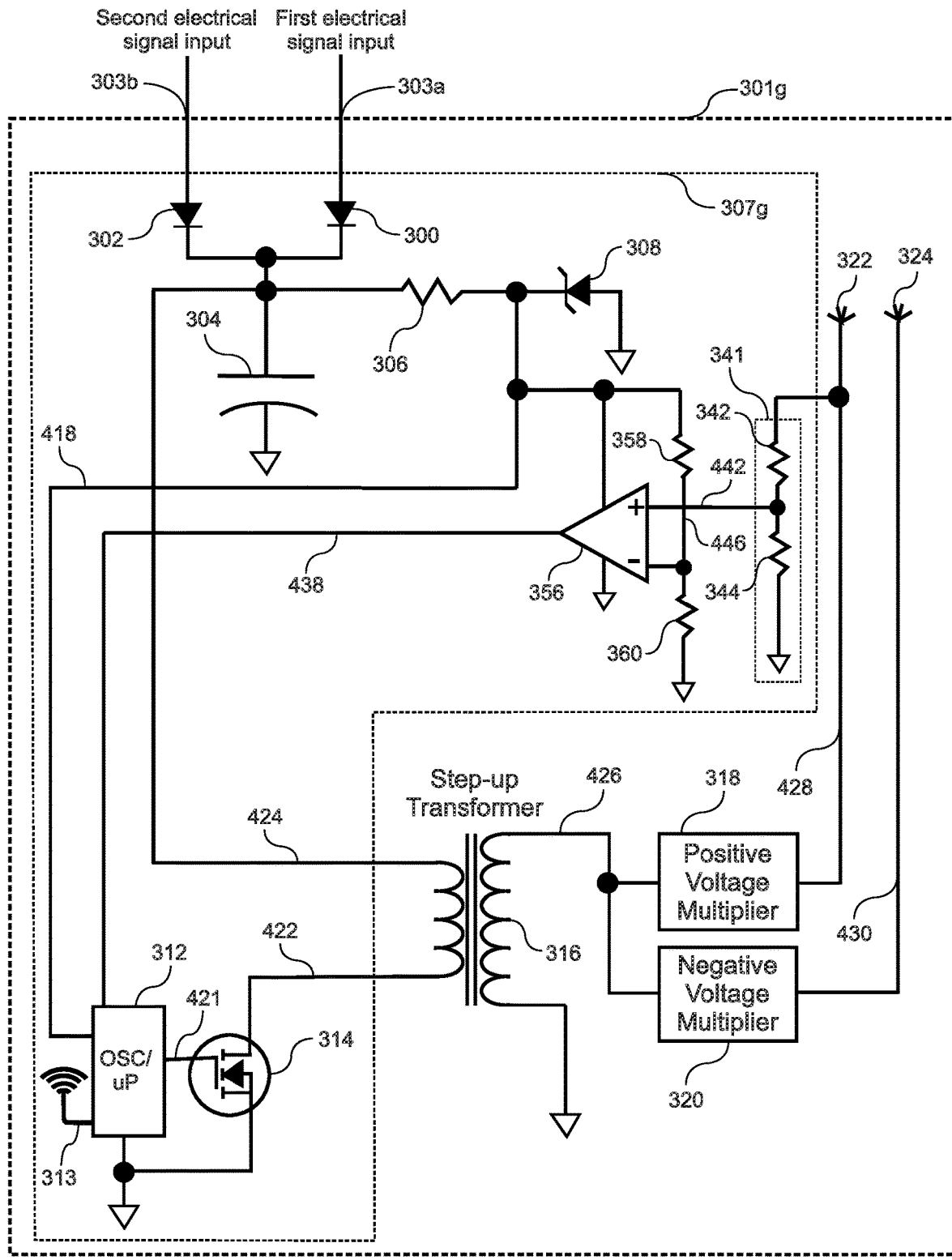
FIG. 7 shows a seventh embodiment of the ionizer with a seventh signal conditioning element including a comparator feedback circuit.

The at least one feedback signal used by the microprocessor 312 is a low-voltage feedback signal (PLFS 432 or NLFS 434 shown in FIG. 3) or a comparator feedback signal (shown in FIG. 7). The PLFS 432 is approximately one one-thousandth of the PDHS or PHO 428 output (1000:1). The NLFS 434 is inverted to a positive signal by the negative voltage feedback circuit 332 and is one one-thousandth of the NDHS or NHO 430 output. The at least one active element processes the PLFS 432 and NLFS 434 from the respective RDN. The active element may be selected from the group consisting of: 1) an operational amplifier (Op Amp) voltage follower (shown in FIG. 5); 2) a second FET voltage follower (shown in FIGS. 6); and 3) a comparator (shown in FIG. 7). FIG. 3 shows a Light Emitting Diode (LED 347) which receives the +5 Volt signal 418. The LED 347 is connected to a LED resistor 349 which is connected to the microprocessor 312. The LED 347 may provide status information or fault alarm messages. The microprocessor 312 also processes the at least one feedback signal and calculates and reports a bipolar ionizer concentration based on the at least one feedback signal.

The first specification for the at least one feedback signal is selected from the group consisting of: (1) an NLFS specification of +1.7V+/−0.4V to +2.5V+/−0.6V for the NLFS 434, (2) a PLFS specification of +1.7V+/−0.4V to +2.5V+/−0.6V for the PLFS 432, (3) a Negative Comparator Feedback Signal (NCFS) specification between 0 and 1 where the NCFS is 1 when the NDHS or NHO 430 is less than the second specification and the NCFS is 0 when NDHS or NHO 430 is greater than the second specification, and (4) a Positive Comparator Feedback Signal (PCFS) specification between 0 and 1 where the PCFS is 1 when the PDHS or PHO 428 is greater than the second specification and the PCFS is 0 when the PDHS or PHO 428 is less than the second specification. The second specification for the at least one DC high-voltage signal is selected from the group consisting of: (1) the NDHS or NHO 430 second specification is −2.5 kV+/−0.6 kV to +1.7 kV+/−0.4 kV, and (2) the PDHS or PHO 428 second specification is +1.7 kV+/−0.4 kV to +2.5 kV+/−0.6 kV.

Figure 4:
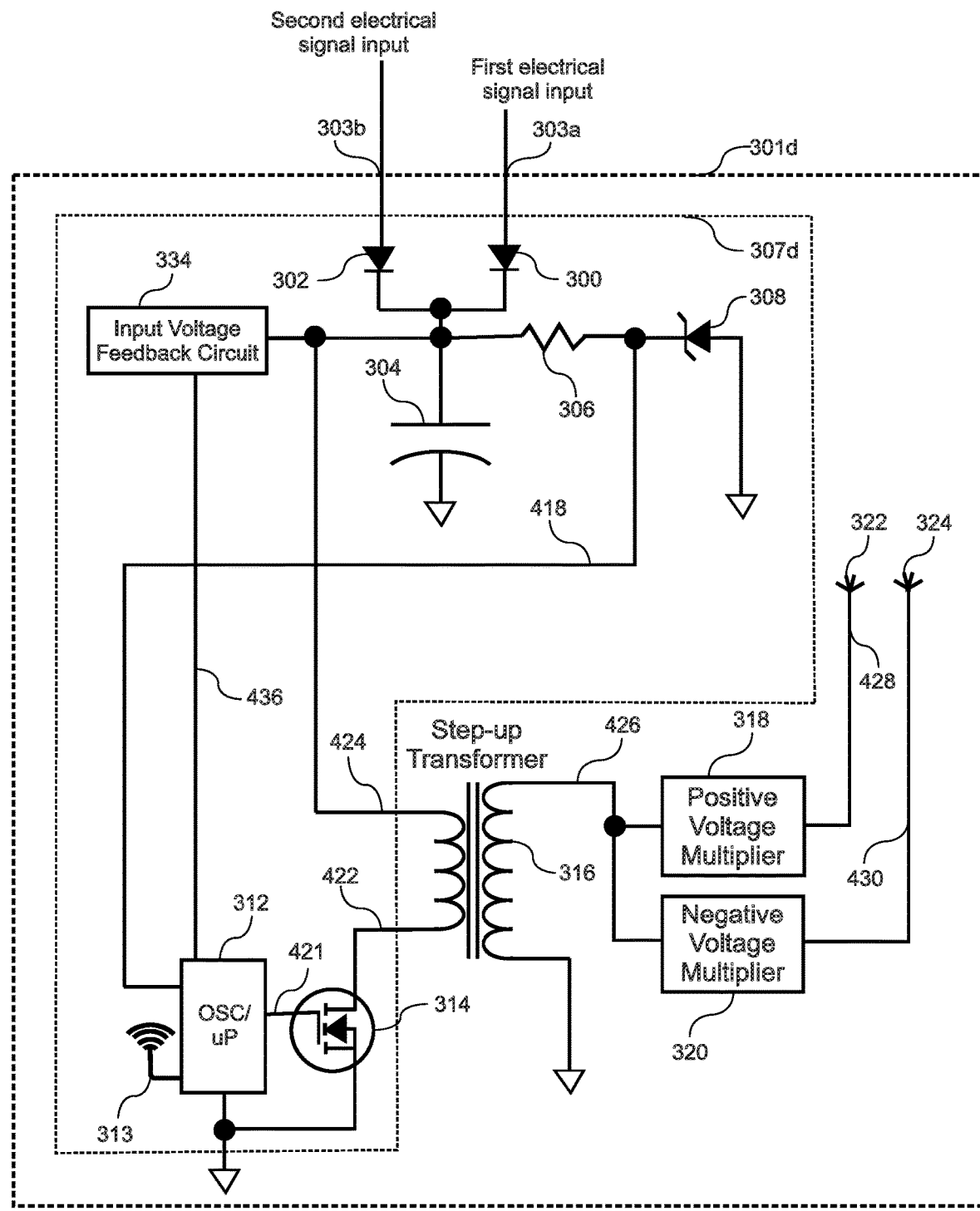
FIG. 4 shows a fourth embodiment of the ionizer with a fourth signal conditioning element with an input voltage feedback circuit

FIG. 4 shows a fourth embodiment of the ionizer 301d including: 1) a fourth signal conditioning element 307d with an input voltage feedback circuit 334, 2) the step-up transformer 316, 3) a positive voltage multiplier 318 connected to a positive-ion electrode 322, and 4) a negative voltage multiplier 320 connected to a negative-ion electrode 324. The fourth signal conditioning element 307d comprises: 1) a first input terminal 303a and a second input terminal 303b, and 2) signal input processing circuit (diodes, resistors, and capacitors), 3) an input voltage feedback circuit 334, and 3) the microprocessor 312 provides a digital signal 421 to a first FET 314 which provides an excitation signal 422 to the step-up transformer 316. Similar to FIG. 2, the first diode 300, the second diode 302, the first capacitor 304, and the first Zener diode 308 are used to create the step-up transformer DC input voltage 424 and the +5 Volt signal 418 from a first or a second electrical signal input. A wireless antenna 313 may be used to provide information regarding the status of the ionizer. As the electrical signal input varies from 20 VAC to 30 VAC, the microprocessor 312 varies the frequency and duty cycle of the digital signal 421 to the first FET 314 and the excitation signal 422 to the step-up transformer 316 which varies the frequency and the duty cycle of the step-up transformer output voltage 426 to produce a high-voltage output ratio less than 80 percent for the PHO 428 and the NHO 430 and a bipolar ion concentration ratio greater than 80 percent from the positive-ion electrode 322 and the negative-ion electrode 324. The input voltage feedback circuit 334 includes a Resistor Divider Network (RDN) to reduce the step-up transformer DC input voltage 424 to an input voltage feedback signal 436 which varies between 0 and +5 VDC (Volts Direct Current) and is approximately one tenth of the step-up transformer DC input voltage 424. The input voltage feedback circuit 334 may be as simple as a low-resistance RDN to provide the input voltage feedback signal 436. Alternatively, the input voltage feedback circuit 334 shown in FIG. 4 may include a high-resistance RDN which contains at least one active element to process the voltage from the high-resistance RDN. The at least one active element may be selected from the group consisting of: an Operational Amplifier (Op Amp) shown in FIG. 5, a second FET shown in FIG. 6, and a feedback comparator shown in FIG. 7.

Figure 5:
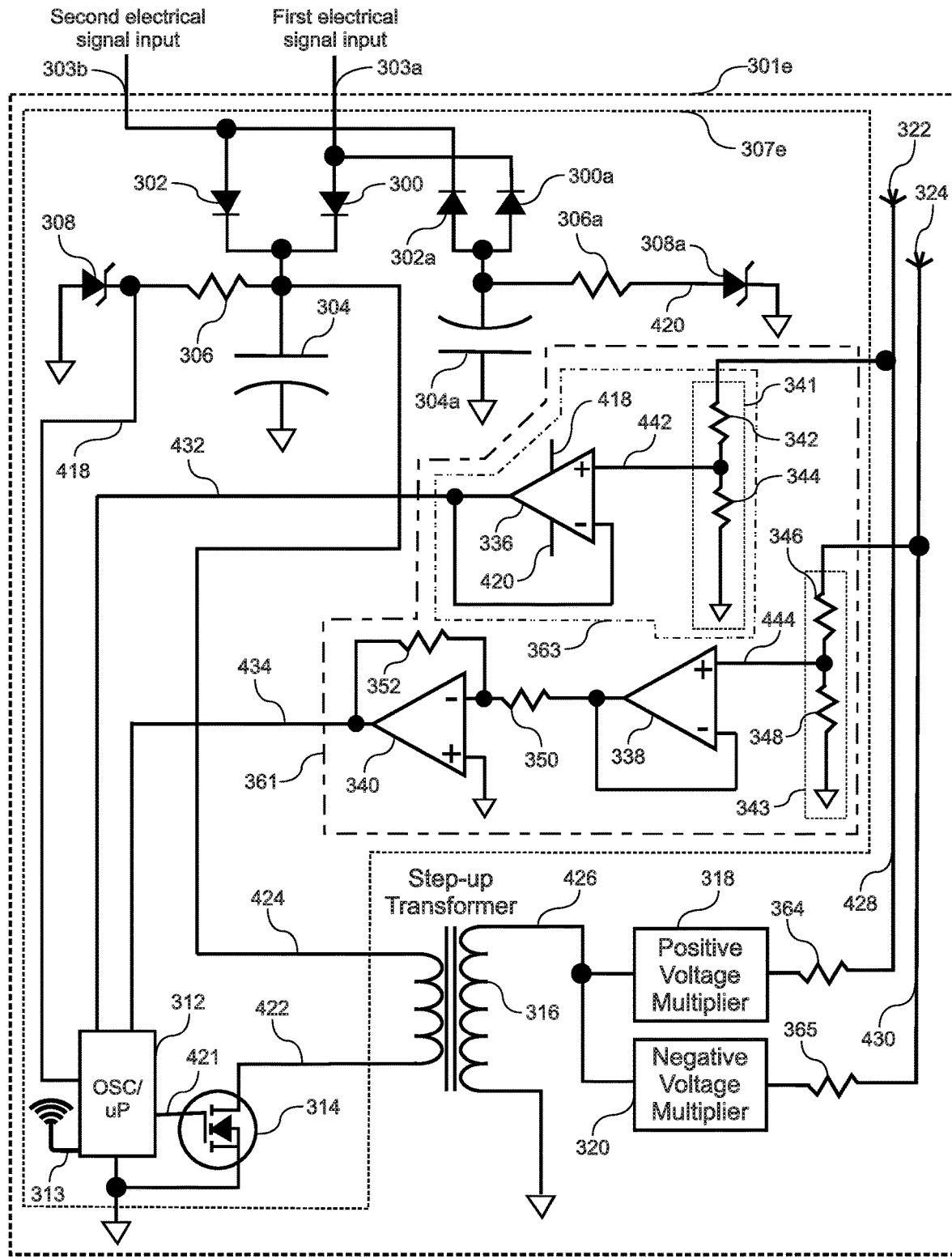
FIG. 5 shows a fifth embodiment of the ionizer with a fifth signal conditioning element with an Operational Amplifier (Op Amp) feedback circuit.

FIG. 5 shows a fifth embodiment of the ionizer 301e including: 1) a fifth signal conditioning element 307e, 2) the step-up transformer 316, 3) a positive voltage multiplier 318 connected to a Positive Electrode Resistor (PER 364) which is also connected to a positive-ion electrode 322, and 4) a negative voltage multiplier 320 connected to a Negative Electrode Resistor (NER 365) which is also connected to a negative-ion electrode 324. The PER 364 and the NER 365 are optionally installed as a safety measure to limit the instantaneous current carried by the positive- and the negative-ion electrodes. The fifth signal conditioning element 307e includes: 1) a first input terminal 303a and a second input terminal 303b, 2) a signal input processing circuit (diodes, resistors, and capacitors), 3) a microprocessor 312 that provides a digital signal 421 to a first FET 314 which provides an excitation signal 422 to the step-up transformer 316, and 4) a feedback circuit 361. The positive voltage multiplier 318 creates the PHO 428 and the negative voltage multiplier 320 creates the NHO 430.

FIG. 5 shows the feedback circuit includes three operational amplifiers (Op Amps) and a positive Resistance Divider Network (positive RDN 341) and a negative RDN 343 to provide feedback from the PHO 428 and the NHO 430 for the microprocessor 312 to modulate the frequency and duty cycle of a digital signal 421 to create the excitation signal 422 to the step-up transformer 316 to provide calibrated unbalanced high-voltage outputs to the positive-ion electrode 322 or the negative-ion electrode 324. The positive RDN 341 is comprised of a positive feedback 100 MΩ resistor 342 a positive feedback 100KΩ resistor 344 connected in series where 100 MΩ refers to 100 Million Ohms and 100KΩ refers to 100 thousand Ohms. The positive RDN 341 reduces the PHO 428 by a ratio of 1000:1 to create a High-impedance Positive Voltage (HPV 442). The negative RDN 343 is comprised of a negative feedback 100 MΩ resistor 346 and a negative feedback 100KΩ resistor 348 connected in series. The negative RDN 343 reduces the NHO 430 by a ratio of 1000:1 to create a High-impedance Negative Voltage (HNV 444). Similar to FIG. 3, a step-up transformer DC input voltage 424 and +5 Volt signal 418 are created from a first electrical signal input supplied to the first input terminal 303a or the second electrical signal supplied to the second input terminal 303b. A first Op Amp 336, a second Op Amp 338, and a third Op Amp 340 receive supply voltages from the +5 Volt signal 418 and the −5 Volt signal 420. The Op Amp is an integrated circuit with two inputs and one output to amplify a weak electrical signal or provide an output voltage difference between two inputs. A wireless antenna 313 may be used to provide status or fault alarm information regarding the balanced bipolar ionizer.

FIG. 5 shows the PLFS 432 is created by a first Op Amp 336 which follows the HPV 442 from the PHO 428. The output from the first Op Amp 336 creates the PLFS 432 sampled by the Analog to Digital (A/D) converter in the microprocessor 312. The first Op Amp 336 draws negligible current and provides a high-input impedance signal to the positive RDN 341 to not interfere with the accuracy of the signal. The second Op Amp 338 creates a low impedance negative voltage signal from the HNV 444 which is inverted to a positive voltage signal by the third Op Amp 340 in series with a first negative feedback 10KΩ resistor 350 and a second negative feedback 10KΩ resistor 352. The output from the third Op Amp 340 creates the NLFS 434 sampled by the A/D converter of the microprocessor 312. Based on the PLFS 432 and/or the NLFS 434 the microprocessor 312 varies the frequency and duty cycle of the digital signal 421 to the first FET 314 to produce a high-voltage output ratio less than 80 percent for the PHO 428 and the NHO 430 and a bipolar ion concentration ratio greater than 80 percent from the positive-ion electrode 322 and the negative-ion electrode 324.

FIG. 5 shows a Positive Electrode Resistor (PER 364) connected between the positive voltage multiplier 318 and the positive-ion electrode 322, and a Negative Electrode Resistor (NER 365) connected between the negative voltage multiplier 320 and the negative-ion electrode 324. The PER 364 and the NER 365 may be optionally installed as a safety measure to limit the instantaneous current carried by the positive- and the negative-ion electrodes. If the PER 364 or the NER 365 are installed, then these resistors may increase the high-voltage output ratio when the high-voltage output ratio is measured at the negative-ion electrode and the positive-ion electrode.

FIG. 5 shows the feedback circuit 361 is comprised of a High-voltage Measurement Circuit (HMC 363). The HMC 363 comprises the positive RDN 341 and the first Op Amp 336 which may be used to measure the high-voltage output ratio where the positive RDN 341 is connected to the emitting end of the positive-ion electrode 322 or the negative-ion electrode 324 and the output from the first Op Amp 336 is measured by a digital multimeter. The measured voltage will represent the high-voltage output divided by the positive RDN value (e.g., approximately 1001:1). If the positive RDN 341 is connected to the emitting end of the positive-ion electrode 322, the voltage from the first Op Amp 336 is a positive voltage output. If the positive RDN 341 is connected to the emitting end of the negative-ion electrode 324, then the voltage output from the first Op Amp 336 is a negative voltage. When measuring the emitting end of the positive-ion electrode 322 with the digital multimeter, the PER 364 would be connected in series with the positive RDN 341. Likewise the NER 365 would be in series when measuring the negative-ion electrode 324. This measurement method is used for data shown in FIG. 8, FIG. 9, and FIG. 10.

The PER 364 resistance reduces the measured voltage from the first Op Amp 336 by the ratio of the PER 364 (or the NER 365) and the positive feedback 100 MΩ resistor 342 plus the positive feedback 100KΩ resistor 344 or the negative feedback 100 MΩ resistor 346 plus the negative feedback 100KΩ resistor 348. The measured high-voltage output reduction fraction (Vrf) may be calculated using Equation 2:

$$Vrf = 1 - [PER364 \text{ or } NER365]/RDN1 \qquad \text{Eq. 2}$$

Where, Vrf=high-voltage output reduction fraction with PER 364 or NER 365 (fraction),
PER 364=resistance of PER 364 (Ohms),
NER 365=resistance of NER 365 (Ohms), and
RDN1=a first RDN1 resistor comprised of a 100 M0 plus 100KΩ resistor or a second RDN2 comprised of a 200 MO plus 100KΩ resistor.

For example, if the PER 364 value is 10 M0, then the high-voltage output reduction fraction from the first Op Amp 336 is approximately 90.01% of the actual output of the positive voltage multiplier 318. If unequal resistance values for the PER 364 and the NER 365 are used, a measurement of the emitting end of the positive-ion electrode 322 compared to the absolute value of a measurement of the emitting end of the negative-ion electrode 324 might produce similar or equal electrode voltages when the absolute value of the electrode voltages might actually be different by 30 to 40 percent. Unequal resistors might be installed between the voltage multipliers and the electrodes for safety or to make it difficult to measure the actual output of the voltage multipliers. The difference in the values of the unequal resistors would not impact the ion generation since the impedance of air is between 1.3 to 3.3 times 10^16 ohms (with ions present) and changes on the order of Mega Ohms (MOs) between the unequal resistors would be insignificant with respect to the impedance of air (resistance of dry air is infinite with no ions present).

FIG. 6 shows a sixth embodiment of the ionizer 301f including: 1) a sixth signal conditioning element 307f, 2) the step-up transformer 316, 3) a positive voltage multiplier 318 connected to a positive-ion electrode 322, and 4) a negative voltage multiplier 320 connected to a negative-ion electrode 324. The sixth signal conditioning element 307f comprises: 1) a first input terminal 303a and a second input terminal 303b, 2) signal input processing circuit (a first diode 300, a second diode 302, a first capacitor 304, a first resistor 306, a first Zener diode 308), 3) a microprocessor 312 and a first FET 314, and 4) a feedback circuit including a second FET 354 and a positive RDN 341. The feedback circuit provides feedback from the PHO 428 for the microprocessor to modulate a frequency and a duty cycle of a digital signal 421 to a first FET 314 which provides an excitation signal 422 to the step-up transformer 316 which varies the frequency and the duty cycle of the step-up transformer output voltage 426 which provides the calibrated unbalanced high-voltage outputs to the positive-ion electrode 322 or the negative-ion electrode 324. A wireless antenna 313 may be used to provide performance information to a software application about the ionizer such as the DC high-voltage signals, the ion concentrations, or electrical faults.

FIG. 6 shows the same signal input processing circuit shown in FIG. 2 to create the step-up transformer DC input voltage 424 and the +5 Volt signal 418 from an electrical power signal. Similar to FIG. 5, the positive RDN 341 is comprised of a positive feedback 100 MΩ resistor 342 and a positive feedback 100KΩ resistor 344 connected in series. The positive RDN 341 reduces the PHO 428 by a ratio of 1000:1 to create the HPV 442. The output from positive RDN 341 is connected to the gate of the second FET 354. The second FET 354 is connected in a voltage follower configuration with the drain connected to the +5 Volt signal 418 and the source connected to a voltage follower load resistor 362. The output from the second FET 354 forms the PLFS 432 sampled by the A/D converter of the microprocessor 312. Based on the PLFS 432, the microprocessor 312 varies the frequency and duty cycle of the digital signal 421 to the first FET 314 to produce a high-voltage output ratio less than 80 percent for the PHO 428 and the NHO 430 to generate a bipolar ion concentration ratio greater than 80 percent from the positive-ion electrode 322 and the negative-ion electrode 324. The RDN and second FET 354 circuit may be duplicated to provide the microprocessor 312 with the NLFS 434 from the NHO 430 (not shown).

FIG. 7 shows a seventh embodiment of the ionizer 301g including: 1) a seventh signal conditioning element 307g, 2) the step-up transformer 316, 3) a positive voltage multiplier 318 connected to a positive-ion electrode 322, and 4) a negative voltage multiplier 320 connected to a negative-ion electrode 324. The seventh signal conditioning element 307g comprises: 1) a first input terminal 303a and a second input terminal 303b, 2) signal input processing circuit (a first diode 300, a second diode 302, a first capacitor 304, a first resistor 306, a first Zener diode 308), 3) a microprocessor 312 (or OSC) and a first FET 314, and 4) a feedback circuit including a positive feedback comparator 356 and a positive RDN 341. The feedback circuit is based on a comparator attached to the positive-ion electrode 322. A wireless antenna 313 may be used to provide information regarding the status of the balanced bipolar ionizer.

FIG. 7 shows the same signal input processing circuit shown in FIG. 2 to create the step-up transformer DC input voltage 424 and the +5 Volt signal 418 from an electrical power signal. Similar to FIG. 5, the RDN is comprised of a positive feedback 100 MΩ resistor 342 and a positive feedback 100KΩ resistor 344 connected in series. The output from the positive RDN 341 is connected to the positive input of a positive feedback comparator 356. The negative input of the positive feedback comparator 356 is connected to a comparator reference voltage 446. The comparator reference voltage 446 is created by two resistors dividing the +5 Volt signal 418. A first positive reference resistor 358 is connected to the +5 Volt signal 418 and the negative terminal of positive feedback comparator 356. A second positive reference resistor 360 is connected to the negative terminal of positive feedback comparator 356 and ground. The comparator circuit may be connected to either the PHO 428 or the NHO 430. FIG. 7 only shows the PHO 428. The comparator circuit compares the output from the RDN to a reference voltage (e.g., 2.5 Volts Direct Current or VDC) and provides the microprocessor 312 with a Positive Comparator Feedback Signal (PCFS 438). The PCFS 438 is a digital 1 if the output from the RDN is greater than 2.5 VDC. The PCFS 438 is a digital 0 if the output from the RDN is less than 2.5 VDC. Based on the PCFS 438, the microprocessor 312 varies the frequency and duty cycle of the digital signal 421 to the first FET 314 which provides an excitation signal 422 to the step-up transformer 316 which varies the frequency and the duty cycle of the step-up transformer output voltage 426 which provides a DC high-voltage output ratio less than 80 percent for the PHO 428 and the NHO 430 and a bipolar ion concentration ratio greater than 80 percent to maintain a comparator signal between 1 and 0. The comparator circuit may be duplicated to provide the microprocessor 312 with a Negative Comparator Feedback Signal (NCFS 439) from the NHO 430 (not shown).

FIG. 8 shows time series measurements of the present invention the bipolar ionizer with a high-voltage output ratio less than 80 percent to generate a bipolar ion concentration ratio greater than 80 percent to eliminate or minimize ozone concentration. The absolute value of the negative DC high-voltage output is 1610 Volts referred to as the NHO 430. The average positive DC high-voltage output is 2030 Volts referred to as the PHO 428. The absolute value of the negative-ion concentration is 70 million ions per cubic centimeter ($10^6$/cc). The average of the positive-ion concentration is 67 million ions/cc. The positive-ion concentration 528 and the negative-ion concentration 530 are sampled using an ion counter that captures a fraction of the total positive and negative-ion concentrations emitted from each electrode. The ion concentration ratios are more important than the magnitude of the ion concentrations. The high-voltage output ratio is 68 percent and the bipolar ion concentration ratio is 96 percent. The ozone concentration measured over 8 hours is zero parts per million (ppm) over a range of 20 to 29.3 VAC electrical signal inputs.

FIG. 9 provides test results of the balanced bipolar ionizer with a high-voltage output ratio less than 80 percent and bipolar ion concentration ratio greater than 80 percent. FIG. 9 provides tests of two embodiments: 1) a positive high-voltage output greater than the absolute value of the negative high-voltage output (rows 1-3); and 2) an absolute value of the negative high-voltage output greater than the positive high-voltage output (rows 4-6). The positive greater than negative high-voltage output tests in rows 1-3 at input voltages of 20 to 29.3 VAC provide zero parts per million (ppm) ozone concentrations over an 8-hour test period (<0.05 ppm). The high-voltage output ratio is 67 to 68% and the bipolar ion concentration ratio is 86 to 96%. The bipolar ion concentration ratio is equal to a minimum of an absolute value of a negative-ion concentration and a positive-ion concentration divided by a maximum of the absolute value of the negative-ion concentration and the positive-ion concentration. The high-voltage output ratio is equal to a minimum of an absolute value of a negative high-voltage output and a positive high-voltage output divided by a maximum of the absolute value of the negative high-voltage output and the positive high-voltage output.

FIG. 9 shows test data for the absolute value of the negative high-voltage output greater than the positive high-voltage output embodiment (rows 4-6). Tests were performed at input voltages ranging from 20 to 29.3 VAC with zero ozone ppmv (<0.05 ppm) over a 24-hour test period. The high-voltage output ratio is less than 80 percent (i.e., 64 to 68%), and the bipolar ion concentration ratio is greater than 80 percent (i.e., 84 to 86%).

FIG. 10 provides laboratory tests of a known prior art bipolar ionizer with high-voltage output greater than or equal to 80 percent and bipolar ion concentration ratio less than 80 percent. The row 7-9 tests at input voltages of 20 to 29.3 VAC provide high-voltage output ratios of 90 to 100 percent, bipolar ion concentration ratios of 66 to 77%, and ozone concentrations of 0.08 to 0.27 ppm. The known prior art ozone concentrations are 1.6 to 5.4 times greater than the CARB and US FDA ozone exposure limit of 0.05 ppm. The voltage measurements shown in FIG. 10 are measured at the emitting end of the positive-ion electrode and the negative-ion electrode. Unequal resistors (PER 364 and NER 365 shown in FIG. 5) may be installed between the voltage multipliers and the electrodes for electrical safety. Unequal resistors may impact the voltage measurements of the high-voltage output at the ends of the positive- or negative-ion emitters. The difference in the values of the unequal resistors would not impact the ion generation since the impedance of air is between 1.3 to 3.3 times 10^16 ohms (with ions present) and changes on the order of Mega Ohms (MOs) between the unequal resistors would be insignificant with respect to the impedance of air (resistance of dry air is infinite with no ions present). The resistance of the unequal resistors may be determined by measuring the high-voltage output from each electrode using a high-voltage measurement circuit shown in FIG. 5 where the RDN is changed for two sets of measurements.

A method of determining an unknown electrode resistor (e.g., PER 364 or NER 365) involves measuring a first voltage V1 with the HMC 363 using the first RDN1 resistor and measuring a second voltage V2 with the HMC 363 using the second RDN2 resistor. The first RDN1 resistor may comprise the positive feedback 100 MΩ resistor 342 and the positive feedback 100KΩ resistor 344. The second RDN2 resistor may comprise a 200 MΩ resistor plus a 100KΩ resistor. Equation 3 is used to determine the value of the PER 364 or the NER 365 resistor based on measurements of the first voltage V1 and the second voltage V2.

$$[PER364 \text{ or } NER365]=[RDN1-Vr(RDN2)]/[Vr-1] \qquad \text{Eq. 3}$$

Where, $Vr=V1/V2$ where the first voltage V1 is measured with the first RDN1 resistor and the second voltage V2 is measured with the second RDN2 resistor, and
RDN2=the second RDN2 resistor comprised of a 200 MΩ plus 100KΩ resistor.

Figure 11:
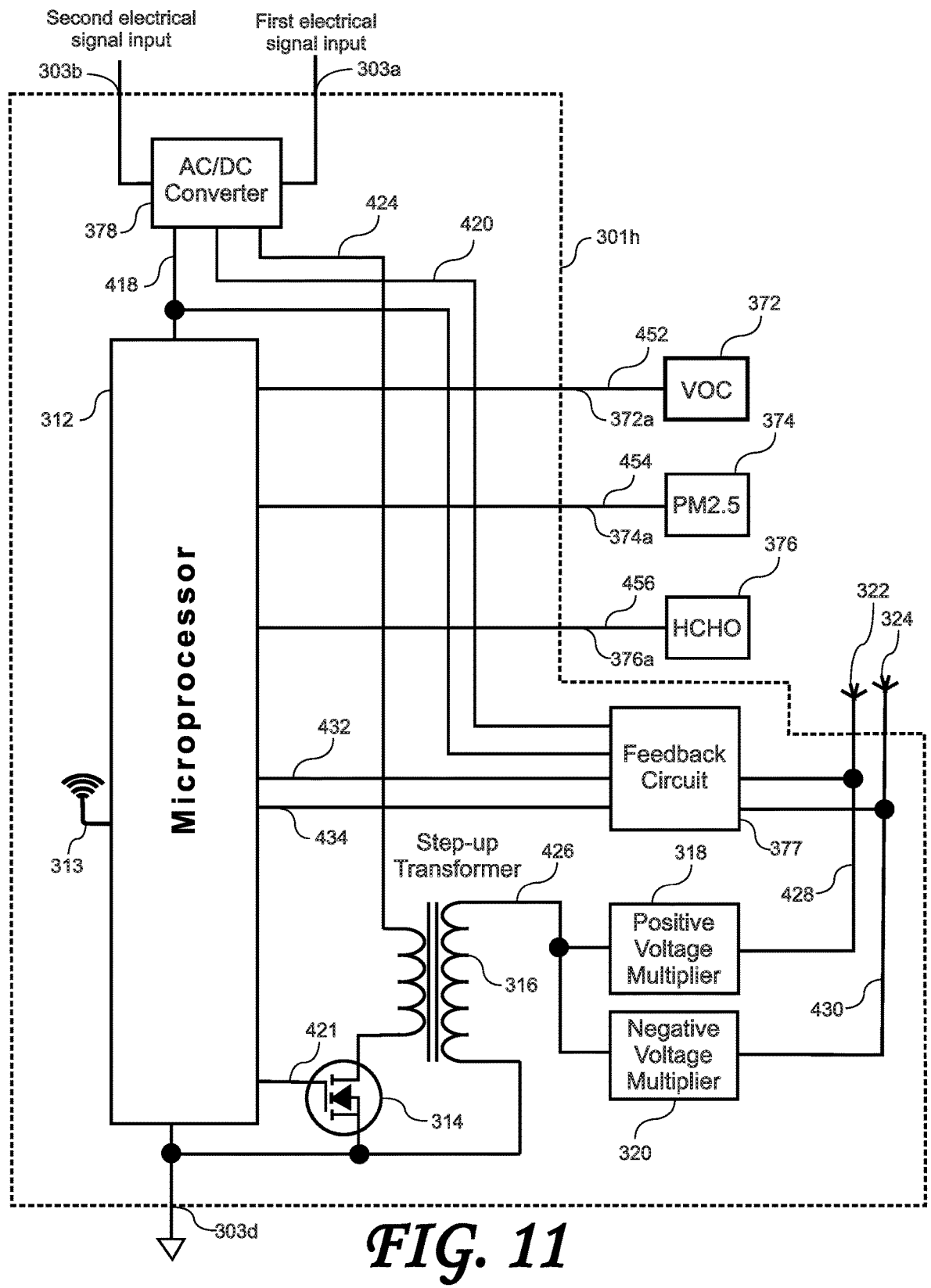
FIG. 11 shows an eighth embodiment of the ionizer including sensors to measure Volatile Organic Compounds (VOCs), Formaldehyde (HCHO), and Particulate Matter less than 2.5 micrometers concentration (a PM 2.5).

FIG. 11 shows an eighth embodiment of the ionizer 301h with at least one Air Quality Monitor (AQM) sensor and a feedback circuit 377. The eighth embodiment shown in FIG. 11 comprises: 1) an AC/DC converter 378, 2) the step-up transformer 316, 3) a positive voltage multiplier 318 connected to a positive-ion electrode 322, 4) a negative voltage multiplier 320 connected to a negative-ion electrode 324, 5) a first input terminal 303a, 6) a second input terminal 303b, 7) a microprocessor 312, 8) a first FET 314, 9) a feedback circuit 377, and at least one sensor selected from the group consisting of: 10) a Volatile Organic Compound sensor or VOC sensor 372, 11) a HCHO sensor 374), and 12) a Particulate Matter less than 2.5 micrometers sensor (a PM 2.5 sensor 376). The AC/DC converter 378 creates the DC voltages required by the ionizer 301h. These voltages are the +5 Volt signal 418, the −5 Volt signal 420, and the step-up transformer DC input voltage 424 to the step-up transformer 316. The positive voltage multiplier 318 creates the PHO 428 and the negative voltage multiplier 320 creates the NHO 430 by multiplying the step-up transformer output voltage 426 from the step-up transformer 316.

FIG. 11 shows the feedback circuit scaling the PHO 428 and NHO 430 to a PLFS 432 and NLFS 434 respectively which are sampled by the microprocessor 312 using the AC/DC converter 378. Based on the PLFS 432 and/or the NLFS 434, the microprocessor 312 varies the frequency and duty cycle of the digital signal 421 to the first FET 314 which provides an excitation signal 422 to the step-up transformer 316, which digital signal 421 varies the frequency and the duty cycle of the step-up transformer output voltage 426 which provides the DC high-voltage output ratio less than 80 percent for the PHO 428 and the NHO 430 and a bipolar ion concentration ratio greater than 80 percent from the positive-ion electrode 322 and the negative-ion electrode 324. FIG. 11 shows three sensors in an airflow serving the bipolar ionizer. The microprocessor 312 monitors the VOC sensor 372 using a first serial communication signal 452 carried on a first serial communication bus 372a. The microprocessor 312 monitors the HCHO sensor 374 using a second serial communication signal 454 carried on a second serial communication bus 374a. The microprocessor 312 monitors the PM 2.5 sensor 376 using a third serial communication signal 456 carried on a third serial communication bus 376a. The AQM may communicate with each sensor using an Inter-Integrated Circuit bus (I2C) and unique addresses for each sensor.

In FIG. 11 the microprocessor 312 consistently maintains the PHO 428 and NHO 430 within the DC high-voltage specification via the modulation and feedback process described above. If the microprocessor 312 detects an elevated concentration of VOCs or HCHO, the microprocessor 312 will de-energize the digital signal 421 to prevent the generation of bipolar ions until the concentration of the VOCs or HCHO is reduced. Also shown is a wireless antenna 313 to communicate using a WIFI (Wireless Fidelity), a Bluetooth (short-range wireless using UHF radio waves in the ISM bands, from 2.402 GHz to 2.480 GHz), or a LPWAN (Low-Power Wide-Area Network with data rates from 0.3 kbit/s to 50 kbit/s per channel). The microprocessor 312 monitors data or information selected from the group consisting of: 1) the PHO 428, 2) the NHO 430, 3) positive ion concentration, 4) negative ion concentration, 5) VOC concentration, 6) HCHO concentration, and 7) PM 2.5 concentration. If the microprocessor 312 detects 1) an elevated concentration of VOCs, HCHO, or PM 2.5, or 2) the PHO 428 or NHO 430 are above or below specifications, and the microprocessor 312 cannot modulate the frequency and/or duty cycle of a digital signal 421 to maintain the bipolar ion concentration within specifications, then the microprocessor 312 may transmit an alarm message using the above wireless communication. If the PHO 428 and NHO 430 regain their specified values, and/or VOCs, HCHO, or PM 2.5 decrease below the threshold specifications, then the microprocessor 312 will send a message indicating that the PHO 428 and NHO 430 or VOCs, HCHO, or PM 2.5 are within specifications.

Figure 12:
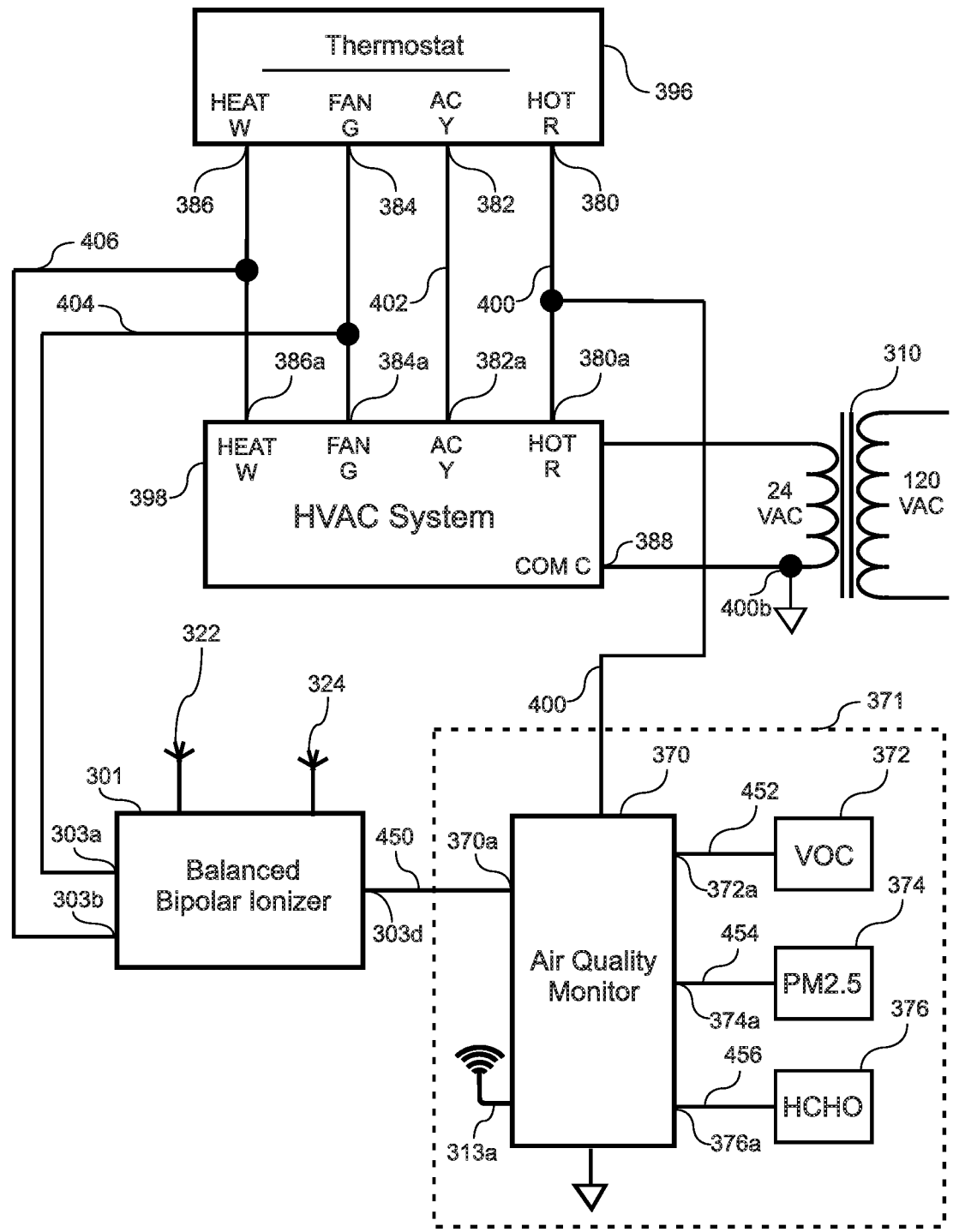
FIG. 12 shows an embodiment comprising: 1) the ionizer, an HVAC system, 3) a thermostat, 4) a 24 VAC transformer, 5) an Air Quality Monitor (AQM), 6) a VOC sensor, 7) a HCHO sensor, and 8) a PM 2.5 sensor.

FIG. 12 shows an embodiment of the ionizer with an AQM system 371 that is not integrated with the ionizer. The embodiment shown in FIG. 12 comprises: 1) an ionizer 301, 2) a HVAC system 398, 3) a thermostat 396, 4) a 24 VAC transformer 310, and 5) and an Air Quality Monitor (AQM) system or AQM system 371 comprising an AQM 370 and at least one sensor selected from the group consisting of: 6) a VOC sensor 372, 7) a HCHO sensor 374, and 8) a PM 2.5 sensor 376. The function of the thermostat 396 and HVAC system 398 are described above. The ionizer 301 may operate with a transformer providing a range of electrical signal inputs selected from the group consisting of: 20 to 30 VAC, 110 to 130 VAC, 210 to 250 VAC, 208 to 280 VAC, 2 to 15 Volts Direct Current (VDC), and 20 to 30 VDC. The control terminal 303d is connected to output 370a of the AQM 370. In one embodiment, the control terminal 303d is connected internally to the Balanced bipolar ionizer ground, shown as a dashed line. In this embodiment, the AQM 370 monitors the VOC sensor 372, the HCHO sensor 374, and the PM 2.5 sensor as described above in FIG. 11. The AQM 370 communicates with the VOC sensor 372 using the first serial communication signal 452 carried on the first serial communication bus 372a. The AQM 370 communicates with the HCHO sensor 374 using the second serial communication signal 454 carried on the second serial communication bus 374a. The AQM communicates with the PM 2.5 sensor 376 using the third serial communication signal 456 carried on the third serial communication bus 376a. An I2C bus may be used as described above.

When the VOC, HCHO, and PM 2.5 concentrations are below the threshold specifications, the AQM shown in FIG. 12 directs the control signal 450 on output 370a to a ground voltage which is equivalent to a signal 400b of the 24 VAC transformer 310. This connection allows current to flow between the at least one ionizer inputs, the first input terminal 303a and the second input terminal 303b and the control terminal 303d and enables the ionizer 301 to generate the positive and/or negative ion concentration using the AC/DC converter 378, the signal conditioning element (not shown), the step-up transformer 316, the Positive Voltage Multiplier (PVM) 318 is connected to the positive-ion electrode 322, and the Negative Voltage Multiplier (NVM) 320 is connected to the negative-ion electrode 324. If the VOC or HCHO concentrations are greater than the threshold specifications (e.g., 0.4 ppmv for VOCs or 0.1 for HCHO), then the AQM 370 may de-energize or adjust the Positive DC High-voltage Signal (PDHS) or the PHO 428 or the negative DC High-voltage Signal or (NDHS) or NHO 430 and not produce or reduce the positive-ion concentration 528 or the negative-ion concentration 530. The AQM 370 may also cause the output 370a to float which stops the flow of current from the first input terminal 303a or the second input terminal 303b causing the bipolar ion generation to cease. Stopping or adjusting the bipolar ion concentration may avoid producing or enhancing concentrations of smaller, potentially oxidized daughter VOCs or HCHO when the VOC or HCHO concentrations are greater than the threshold levels.

In another embodiment of FIG. 12, the control terminal 303d is connected internally to the microprocessor 312, shown as a second dashed line and the ground of the ionizer 301 is connected to the signal 400b of the 24 VAC transformer 310. The AQM 370 monitors the sensors as described above, but in this embodiment, the control signal 450 may be a digital or analog control signal sent by the AQM 370 using output 370a to the control terminal 303d to the microprocessor 312 indicating the levels of VOCs or HCHO. The microprocessor 312 processes the control signal 450 to de-energize or reduce a positive and/or negative DC high-voltage output as described above. The AQM 370 is shown with an optional wireless antenna 313a to communicate data and/or messages to a user using a software application (APP). Data may include concentrations of VOC, HCHO, and/or PM 2.5 or DC high-voltage signals on the electrodes or bipolar ion concentrations.

Figure 13:
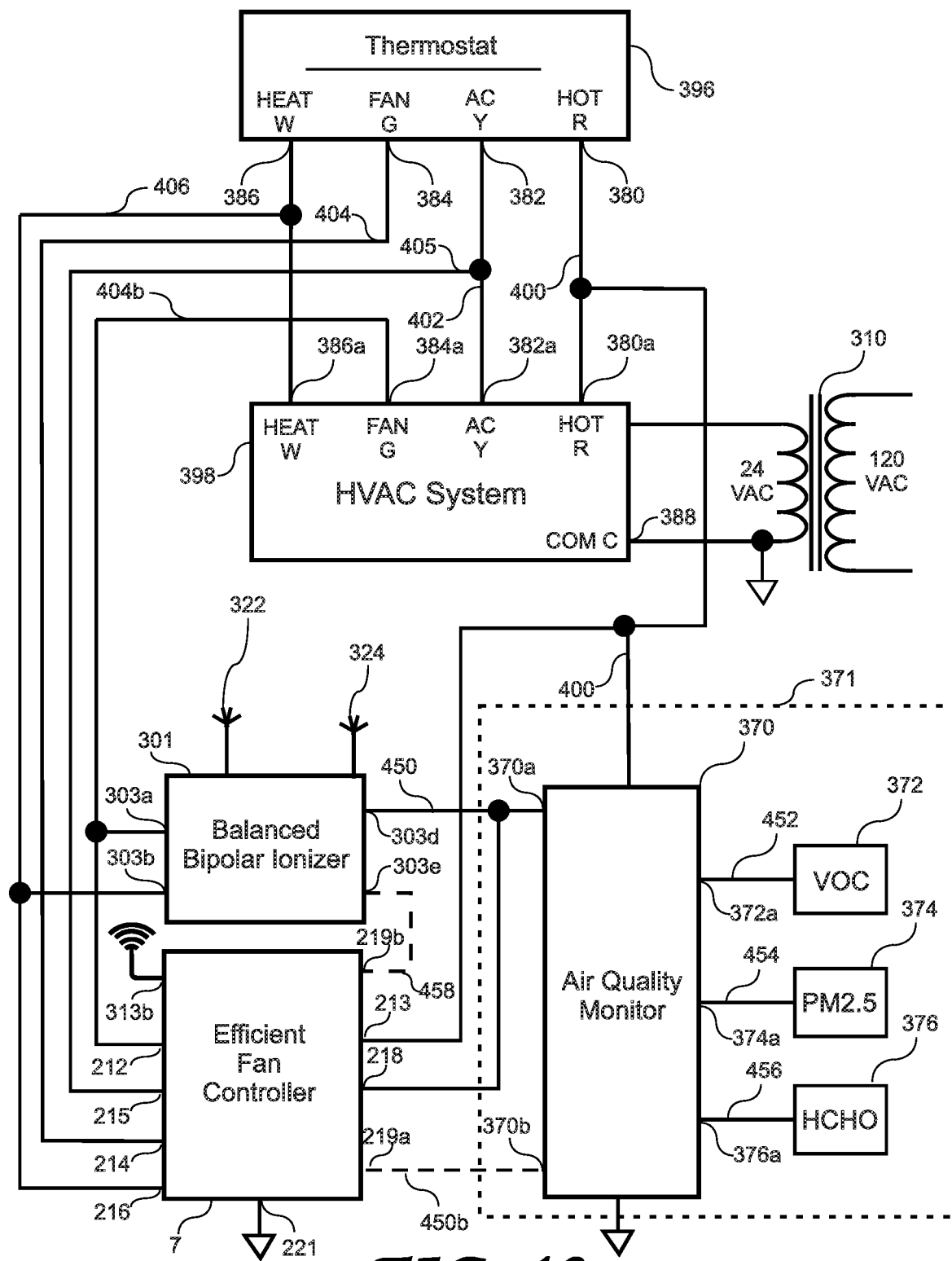
FIG. 13 shows an embodiment comprising: 1) the ionizer, 2) the HVAC system, 3) the thermostat, 4) a 24 VAC transformer, 5) an Efficient Fan Controller (EFC), and 6) an Air Quality Monitor (AQM) system comprising an ACM and at least one sensor selected from: 7) a VOC sensor, 8) a HCHO sensor, and 9) a PM 2.5 sensor.

FIG. 13 shows an embodiment of a system including 1) the ionizer 301, 2) HVAC system 398, 3) a thermostat 396, 4) a 24 VAC transformer 310, 5) an Efficient Fan Controller (EFC) 7, and 6) and an AQM system 371 comprising 7) an AQM 370 and at least one sensor selected from the group consisting of: 8) a VOC sensor 372, 9) a HCHO sensor 374, and 10) a PM 2.5 sensor 376. The ionizer 301 could be embodied as described in FIG. 12 with the addition of an ion concentration output 303e used to communicate an ion concentration using a fifth serial communication signal 458 to the EFC 7 using an ion concentration input 219b. The thermostat 396 and the HVAC system 398 are described above. In this embodiment the ionizer 301 and the AQM 370 function similar to FIG. 12. The EFC 7 receives control signals from the thermostat 396. A heat W input 216 receives a heat W signal 406 from a heat W terminal 386. A fan G input 214 receives a fan G signal 404 from a fan G terminal 384. An AC Y input 215 receives an AC Y signal 405 from an AC Y terminal 382. A hot R input 213 receives a hot R signal 400 from hot R terminal 380. A Common (a COM C input 221) is connected to the COM C terminal (ground connection) of the 24 VAC transformer 310. The EFC 7 provides a fan G signal 404b from a fan G signal output 212 of the EFC 7 to a fan G terminal 384a of the HVAC system 398 and the fan G input or the first input terminal 303a of the ionizer 301. The HVAC system 398 also receives a heat W signal from the heat W terminal 386 to the heat W terminal 386a, an AC Y signal from the AC Y terminal 382 to the AC Y terminal 382a, a hot R signal from the hot R terminal 380 to the hot R terminal 380a, and a COM C terminal 388 is connected to the COM C of the 24 VAC transformer 310.

The EFC 7 shown in FIG. 13 performs data processing and wireless communication using a wireless antenna 313b.

The data processing and wireless communication functions may also be embodied in the ionizer 301. The VOC, the HCHO, and the PM 2.5 concentrations are transmitted from the AQM concentration output 370b of the AQM 370 to the AQM concentration input 219a using a fourth serial communication signal 450b. The EFC 7 also monitors the status of the control signal 450 through the common monitor input 218. If the common monitor input 218 is at the common voltage level, the ionizer 301 is powered and generating ions unless otherwise faulted. If the common monitor input 218 is not at the common voltage, the ionizer 301 is either de-energized or adjusting a positive and/or negative DC high-voltage output to stop generating or reduce the ion concentration as described above. The ion concentration output 303e is connected to the ion concentration input 219b and the ion concentration levels are communicated using the fifth serial communication signal 458. The EFC 7 (or ionizer 301) performs data processing and wireless communication using a wireless antenna 313b to periodically transmit at least one measurement selected from the group consisting of: 1) the PHO 428, 2) the NHO 430, 3) positive ion concentration, 4) negative ion concentration, 5) VOC concentration, 6) HCHO concentration, and 7) PM 2.5 concentration.

Figure 14:
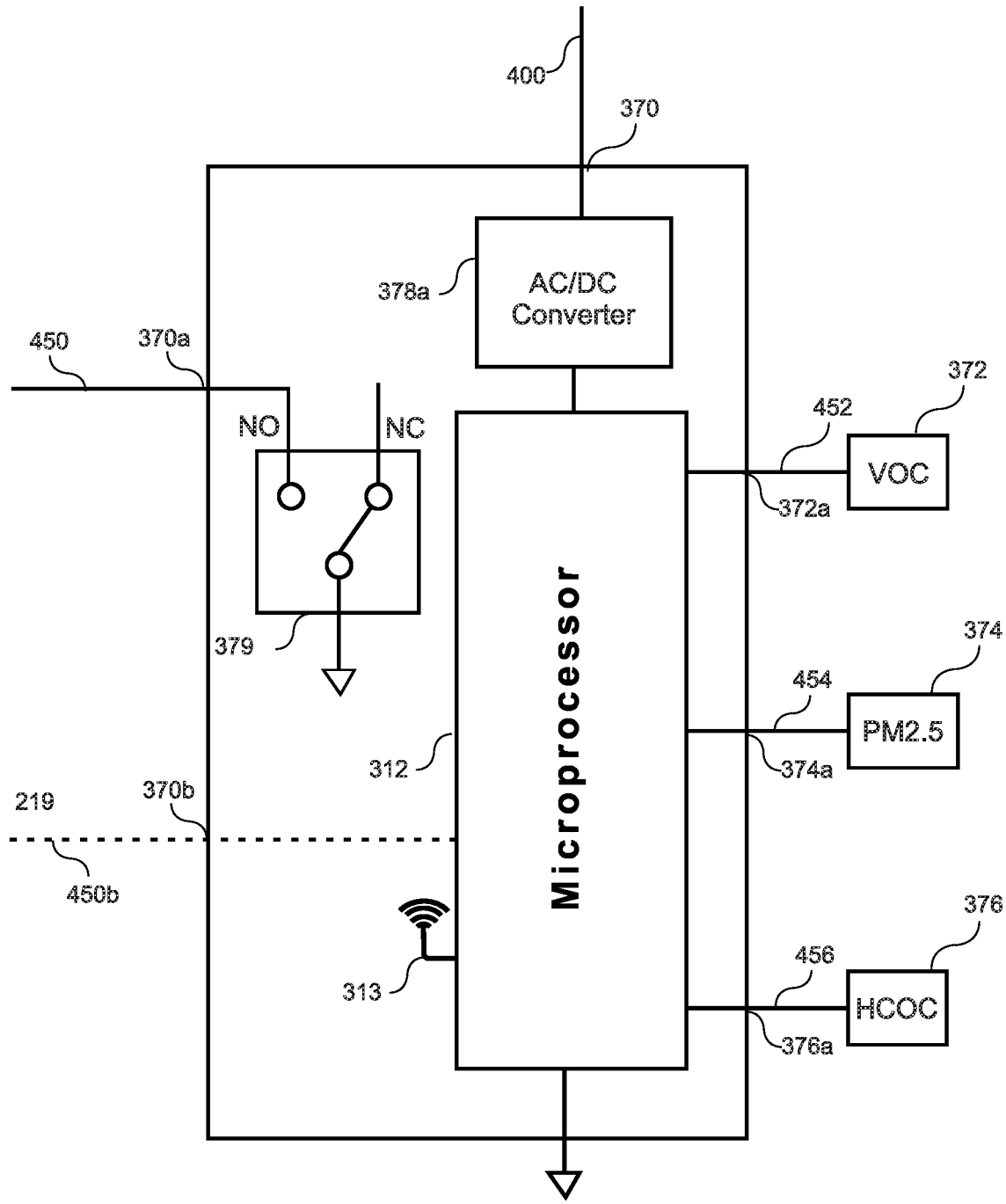
FIG. 14 shows an embodiment with an AQM system used to control the balanced bipolar ionizer, where the ACM comprises 1) a microprocessor, 2) an Alternating Current/Direct Current (AC/DC) converter, 3) a switch, and at least one sensor selected from the group consisting of: 4) a VOC sensor, 5) a HCHO sensor, and 6) a PM 2.5 sensor.

FIG. 14 shows an embodiment of an AQM system 371 used to control the ionizer 301 comprising: 1) an AQM 370 comprising, 2) a microprocessor 312, 3) an AC/DC converter 378a, 4) a switch 379 or Digital to Analog Converter (DAC), and at least one sensor selected from the group consisting of: 5) a VOC sensor 372, 6) a HCHO sensor 374, and 7) a PM 2.5 sensor 376. The AC/DC converter 378a provides power to the microprocessor 312 and to the sensors. The microprocessor 312 monitors the VOC sensor 372, the HCHO sensor 374, and the PM 2.5 sensor 376 as described above. When the VOC, HCHO, and PM 2.5 concentrations are within specifications, the microprocessor 312 uses the switch 379 or DAC to provide a control signal 450. In one embodiment, the control signal 450 may be a ground voltage which is equivalent to the signal 400b of the 24 VAC transformer 310 (see FIG. 13). This control signal 450 allows current to flow between the at least one balanced bipolar ionizer inputs, the first input terminal 303a and the second input terminal 303b which allows the ionizer 301 to generate the positive-ion concentration 528 and/or the negative-ion concentration 530 (see FIG. 13). If the VOC or HCHO concentration in an airflow serving the ionizer 301 exceeds specifications, then the microprocessor 312 may use the switch 379 or DAC to provide a control signal 450 on the output 370a which may be proportional to the VOC concentration. The ionizer 301 processes this signal and either de-energizes or reduces the positive and/or negative DC high-voltage signal to not produce or to adjust the positive and/or negative ion concentration. The microprocessor 312 may also use the switch 379 or DAC to cause the control signal 450 to float where the ionizer 301 is de-energized or where the control signal 450 is used to reduce the positive and/or the negative ion concentration. For the switch 379, the microprocessor 312 may de-energize switch 379 and cause the control signal 450 to float. The switch 379 or DAC may be replaced with a method of serial communication to provide VOC levels to the ionizer 301. The microprocessor 312 provides WIFI communication using a wireless antenna 313.

Figure 15:
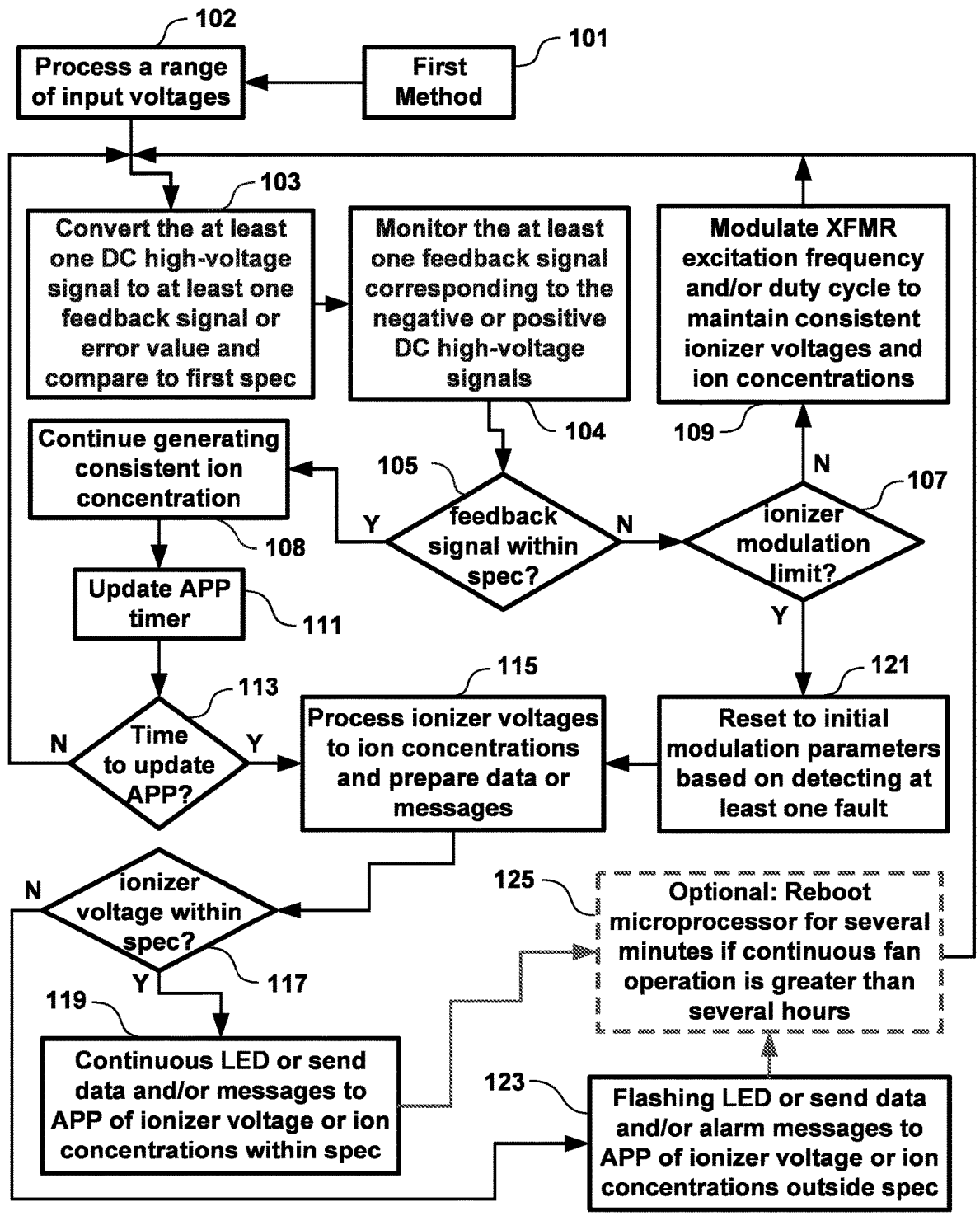
FIG. 15 shows a first method to control the ionizer to maintain a consistent Direct Current (DC) high-voltage output and consistent ion concentration to minimize ozone concentration to zero parts per million by volume (ppmv) over a range of input voltages.

FIG. 15 shows a first method 101 to control the ionizer to maintain a consistent unbalanced DC high-voltage output ratio and generate a balanced bipolar ion concentration ratio to minimize an ozone concentration to zero parts per million by volume (ppmv) over a range of input voltages. Depending on the transformer, the range of input voltages may vary from: 20 to 30 VAC, 110 to 130 VAC, 210 to 250 VAC, 208 to 280 VAC, 2 to 15 VDC, or 20 to 30 VDC. Step 102 processes the input voltages. Step 103 converts the at least one DC high-voltage signal to at least one feedback signal or error value and compares the at least one feedback signal or error value to a first specification (spec) corresponding to the ionizer voltage to determine whether the at least one feedback signal is within the first specification (described above). Step 104 monitors the at least one feedback signal corresponding to the negative and/or positive DC high-voltage signals. If step 105 is Yes (Y), and the at least one feedback signal is within the first specification or ionizer voltage (NDHS or NHO and/or PDHS or PHO), then the method proceeds to step 108 to continue generating the consistent ion concentration and proceeds to step 111 to an APP update timer where the frequency of APP update messages is controlled by step 113 which checks whether or not it is time to update the APP. If step 113 is Yes (Y), the method proceeds to step 115 to process the ionizer voltages to report ion concentrations and prepare data or messages. After step 113, if NO (N), the method loops back to step 103.

Per FIG. 15, if the at least one feedback signal or error value corresponding to the ionizer voltages are not within the first specification (spec) at step 105, then the method proceeds to step 107. At step 107, the method determines if the microprocessor 312 has reached an ionizer modulation limit where the microprocessor 312 can no longer modulate the digital signal 421 to a first FET 314 which provides an excitation signal 422 to the step-up transformer 316 which varies the frequency and the duty cycle of the step-up transformer output voltage 426 which provides the specified the ionizer voltages on the electrodes. If step 107 determines that the ionizer modulation is No (N) where the microprocessor has not reached a modulation limit, then the method proceeds to step 109. At step 109 the method modulates the XFMR (i.e., step-up transformer) excitation frequency and/or duty cycle of the digital signal 421 as described above which provides the DC high-voltage signal and maintains consistent ionizer voltages and ion concentrations. After step 109, the method loops back to step 103. As described above, the microprocessor varies the frequency and duty cycle of the digital signal to control the excitation signal for the step-up transformer (XFMR) and modulate the frequency and the duty cycle of the step-up transformer output voltage to consistently maintain the at least one DC high-voltage signal and generate a consistent ion concentration over a range of electrical signal inputs.

If step 107 of FIG. 15 is Yes (Y) where the ionizer modulation limit has been reached in step 107, then the method proceeds to step 121 and resets to initial modulation parameters using an algorithm to begin the method from an initial state. The modulation limits of the frequency and/or duty cycle may vary depending on the transformer magnetics. In one embodiment, the modulation limit frequency may be less than 8 kHz and the duty cycle may be equal to 0 percent. In another embodiment, the frequency may be greater than 12 kHz and the duty cycle may be equal to 100 percent. For this case the method is within the modulation limit when the frequency is between 8 to 12 kHz and duty cycle less than 100 percent. A modulation limit may be reached based on at least one fault selected from the group consisting of: an electrical short on the positive-ion electrode or the negative-ion electrode, a power supply voltage input fault beyond a specified range of 20 to 30 VAC, a power supply or transformer failure, an electronic component failure; and providing at least one message selected from the group consisting of: a text message, an email message, an audio communication, a voice mail message, or a wireless communication method. Faults are identified in step 123 by a flashing LED or sending data and/or an alarm message to a user. After step 121, the method proceeds to step 115 to process the ionizer voltages to ion concentrations and prepare data or messages.

After step 115 of FIG. 15, the method proceeds to step 117 to check if the ionizer voltages are within spec again, to determine which type of messages are to be sent to a user. If step 117 is No (N) where the ionizer voltages are not within spec, then the method proceeds to step 123 to provide a flashing LED lamp indicator or to send data and/or alarm messages to the APP (software) of ionizer voltages or ion concentrations outside the spec. If step 117 is Yes (Y) where the ionizer voltages are within the spec, then the method proceeds to step 119 to provide a continuous LED lamp indicator or send data and/or messages to the software application (APP) of ionizer voltages or ion concentrations within spec. The data and/or alarm messages may be sent to a user using at least one communication method selected from the group consisting of: a graphical display, a text message, an email message, an audio communication message, a voice mail message, or a wireless communication method. The wireless communication may use a cellular system, a WIFI (wireless fidelity), a Bluetooth (short-range wireless using UHF radio waves in the ISM bands, from 2.402 GHz to 2.480 GHz), a Low-Power Wide-Area Network (LPWAN with data rates from 0.3 kbit/s to 50 kbit/s per channel), or an ultra-low power Long-range Radio (LoRa) or LoRa Wide Area Network (LoRaWAN) communication protocol. After step 119 or step 123, the method loops back to step 103 to continue monitoring the positive and/or negative ionizer electrode voltages. Step 125 provides an optional reboot of the microprocessor of the ionizer for several minutes if continuous fan operation is greater than several hours to enhance the ionizer lifetime and clear accumulated errors in the microprocessor memory to improve performance of the microprocessor and the ionizer.

Figure 16:
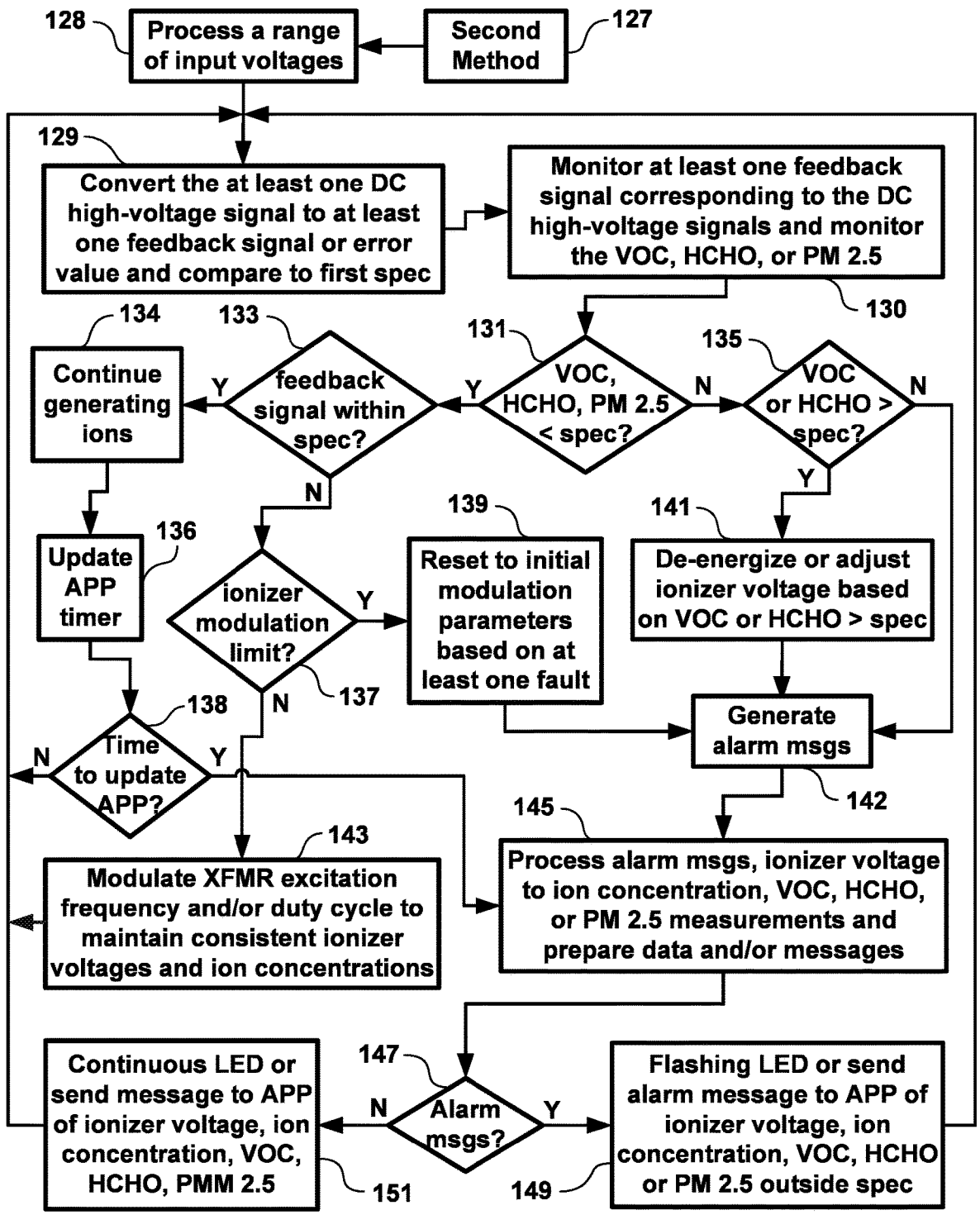
FIG. 16 shows a second method to perform a similar control as the first method while also providing a control to de-energize the ionizer based on at least one Indoor Air Quality (IAQ) concentration selected from: a VOC concentration, a HCHO concentration, or a PM 2.5 concentration.

FIG. 16 shows a second method 127 to perform a similar control as the first method 101 while also providing a control to de-energize the ionizer based on at least one Indoor Air Quality (IAQ) concentration selected from the group consisting of: a Volatile Organic Compound (VOC) concentration (parts per million or ppm), a formaldehyde (HCHO) concentration in ppm, or a Particulate Matter less than 2.5 micrometers concentration (a PM 2.5). The ionizer de-energizes or reduces the positive and/or negative DC high-voltage signal to not produce or reduce a positive and/or negative ion concentration when the VOC or HCHO concentrations are greater than the spec. The spec may be a first threshold value for a VOC or second threshold value for a HCHO. The first threshold of the spec may comprise a Permissible Exposure Level (PEL) of 0.75 ppmv and an action level of 0.4 ppmv for a VOC per the US Department of Housing and Urban Development (HUD) level for residential mobile homes. The second threshold of the spec may comprise a 0.1 ppmv for HCHO per OSHA. The method may comprise adjusting the ion concentration energy below an energy threshold that does not disassociate VOCs to daughter VOCs (i.e., less than 9 electron Volts (eV) or another eV threshold).

FIG. 16 step 128 processes a range of input voltage (e.g., 20 to 30 VAC, etc.). At step 129 the method converts the at least one DC high-voltage signal to at least one feedback signal or error value and compares the at least one feedback signal or error value to the first specification (described above). At step 131 the method monitors the at least one feedback signal corresponding to the DC high-voltage signal (e.g., the positive and/or negative ionizer electrode voltage), VOC, HCHO, and PM 2.5, and proceeds to step 131. If step 131 is Yes (Y) the VOCs, PM 2.5 and HCHO concentrations are within specification, the method proceeds to step 133. At step 133, if the at least one feedback signal or error value are within the first specification (described above), then the method continues to step 134 and continues generating ions. At step 136, the method updates an APP update timer with a software application and continues to step 138. If step 138 is No (N) the time to update the APP has not expired, then the method loops back to step 129. If step 138 is Yes (Y), the time to update APP is expired, then the method proceeds to step 145 to process alarm messages, ionizer voltages to ion concentrations, VOC, HCOC, and PM 2.5 measurements and prepare data and/or messages and proceeds to step 147. If no alarms are generated and step 147 is No (N), then the method proceeds to step 151 to continue providing a continuous LED lamp indicator or to send a message to the APP (software) regarding the ionizer voltages, ion concentrations, VOC, HCOC and/or PM 2.5 concentrations. The message may be sent using at least one communication method selected from the group consisting of: a graphical display, a text message, an email message, and an audio communication message. After step 151, the method loops back to step 129.

If step 133 of FIG. 16 is No (N), the method proceeds to step 137 and checks the ionizer modulation limit (upper or lower) where the microprocessor 312 cannot modulate the digital signal 421 to a first FET 314 to the step-up transformer 316 to achieve the first specification corresponding to the second specification of the positive and/or negative ionizer electrode voltage output (the spec is +1.7 kV+/−0.4 kV to +2.5 kV+/−0.6 kV on the positive-ion electrode 322 and −2.5 kV+/−0.6 kV to −1.7 kV+/−0.4 kV on the negative-ion electrode 324). If step 137 is No (N) and the ionizer voltages are not within spec and the ionizer modulation is not reached, then the method proceeds to step 143 and modulates the transformer (XFMR) excitation frequency and/or duty cycle to maintain consistent ionizer voltages and ion concentrations and the method loops back to step 129. If step 137 is Yes (Y) where the ionizer modulation limit is reached, then the method proceeds to step 139 to reset the modulation parameters as described above.

After step 139 of FIG. 16, the method goes to step 142 to generate an alarm message, then to step 145 to process the alarm message, and then to step 147. If step 147 is Yes (Y), the method proceeds to step 149 to send the alarm message using a flashing LED or the APP (software) and sends the ionizer voltage and ion concentrations using the at least one communication method, and loops back to step 129. If step 135 is No (N) the method proceeds to step 142 to generate a PM 2.5 alarm without de-energizing the ionizer voltage (in step 141 which is skipped). If step 135 is Yes (Y), then the method proceeds to step 141 to de-energize or reduce the positive and/or negative DC high-voltage signal to not produce or reduce a positive and/or negative ion concentration when the VOC or HCHO concentrations are greater than the spec. After step 141 the method proceeds to step 142 to generate alarm messages and proceeds to step 145 to process the alarm messages and prepare data and/or messages. After step 145, the method proceeds to step 147. If step 147 is Yes (Y), then the method continues to step 149 to provide a flashing LED or send an alarm message to the software application (APP) of ionizer voltages, ion concentrations, VOC, HCHO or PM 2.5 concentrations and loops back to step 129. After step 149 or step 151, the method returns to step 129 to continue the second method. Alternatively, the method may provide an optional step (not shown) to reboot the microprocessor of the ionizer for several minutes if continuous fan operation is greater than several hours to enhance the ionizer lifetime and performance (see step 125 in FIG. 15).

Figure 17:
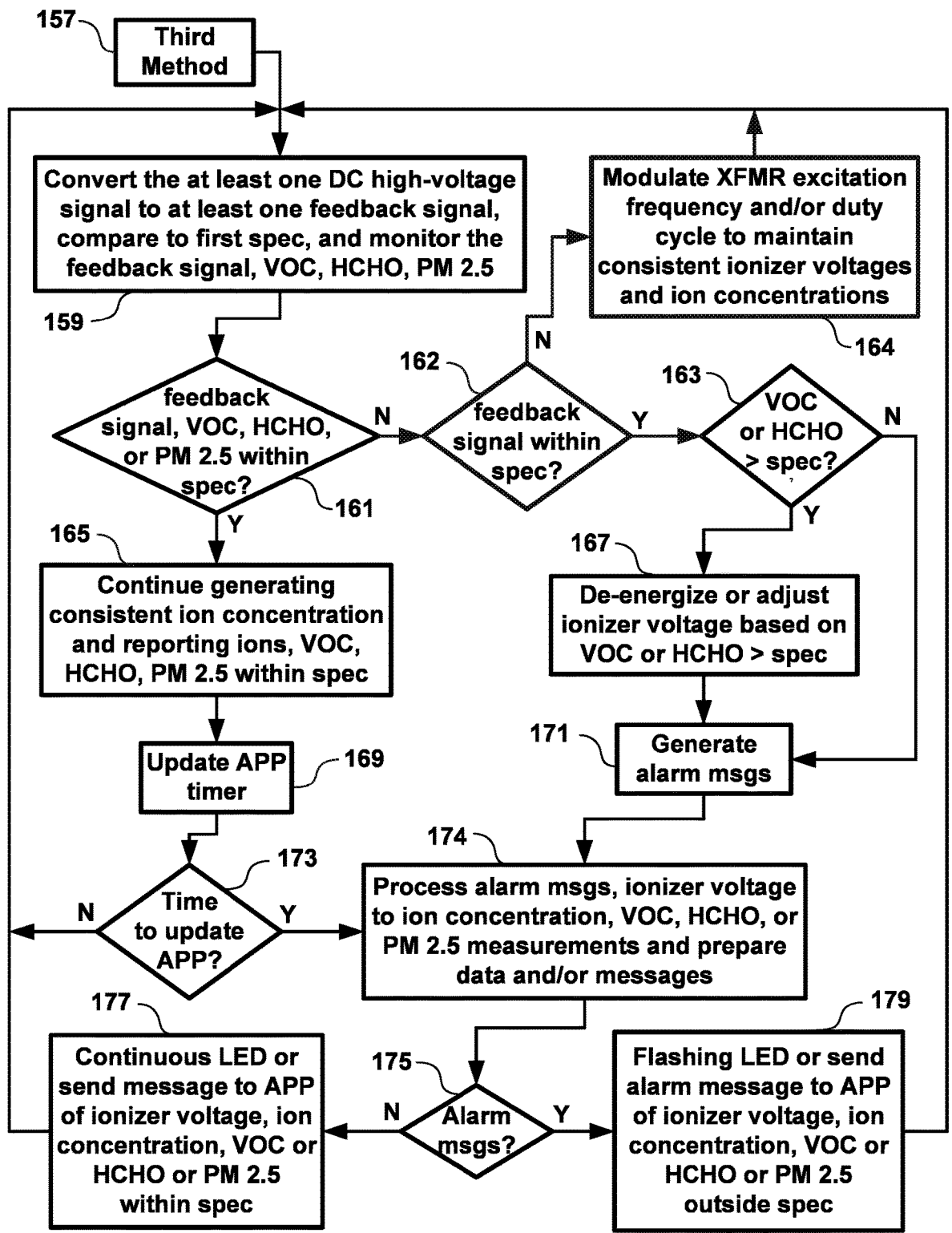
FIG. 17 shows a third method for de-energizing the ionizer when the concentration of VOCs or HCHO is above a threshold specification limit.

FIG. 17 shows a third method 157 for de-energizing the digital signal 421 to a first FET 314 to the step-up transformer 316 if the concentration of VOCs or formaldehyde (HCHO) is greater than a spec (e.g., a threshold specification of 0.40 ppmv for VOCs and 0.1 ppmv for HCHO). Step 159 converts the at least one DC high-voltage signal (e.g., positive and/or negative ionizer electrode voltage) to at least one feedback signal or error value used by the microprocessor 312 to monitor the ionizer voltage and compare to the specification for the ionizer voltage. Step 159 also monitors VOC, HCHO, or PM 2.5 concentrations with a VOC sensor 372, a HCHO sensor 374, or a PM 2.5 sensor 376 and proceeds to step 161. If step 161 is Yes (Y), the at least one feedback signal is within the first specification and the VOCs, PM 2.5 and HCHO concentrations are within specification. The method then goes to step 165 to generate or continue generating the ion concentration and reports the ion concentration is within the second specification and the VOC, the HCHO, and the PM 2.5 concentrations within specifications. The method continues to step 169 to update the APP timer, and step 173 to check time to update the APP. If step 173 is No (N) the method loops back to step 159. If step 173 is Yes (Y), the method continues to step 174 to process alarm messages, ionizer voltages to ion concentrations, VOC, HCHO and PM 2.5 measurements and prepare data and/or messages as described above.

If step 161 of FIG. 17 is No (N), the method goes to step 162 to check if the at least one feedback signal is within the first specification. If No (N), the method goes to step 164 and modulates the XFMR (i.e., step-up transformer) excitation frequency and/or duty cycle of the digital signal as described above which provides the DC high-voltage signal and maintains consistent ionizer voltages and ion concentrations. Not shown are steps where the ionizer modulation limit is reached or the modulation parameters are reset where the method skips step 164 and loops back to step 159. After step 164, the method loops back to step 159. If step 162 is Yes (Y), the method goes to step 163 where the method checks if the VOC or the HCHO concentrations are greater than the specification (spec). If step 163 is No (N) the method proceeds to step 171 to generate a PM 2.5 alarm without de-energizing the ionizer voltage (in step 167 which is skipped). If step 163 is Yes (Y), then the method proceeds to step 167 de-energize or adjust the ionizer voltage based on the VOC or HCHO levels being greater than the specification as described above. After step 167 the method proceeds to step 171 to generate alarm messages and proceeds to step 174 to process the alarm messages and prepare data and/or messages and proceeds to step 175. If step 175 is Yes (Y), the method goes to step 179 to provide a flashing LED or send an alarm message to a software application (APP) of ionizer voltage and ion concentrations, VOC, HCHO or PM 2.5 concentrations and loops back to step 159 to continue. If step 175 is No (N), the method proceeds to step 177 to provide a continuous LED signal or send a message to the APP of ionizer voltage, ion concentration, VOC, HCHO, or PM2.5 concentration within specifications. After step 177 or step 179, the method returns to step 159 to continue the third method. Alternatively, the method may provide an optional step (not shown) to reboot the microprocessor of the ionizer for several minutes if continuous fan operation is greater than several hours to enhance ionizer life and performance (see step 125 in FIG. 15).

Figure 18:
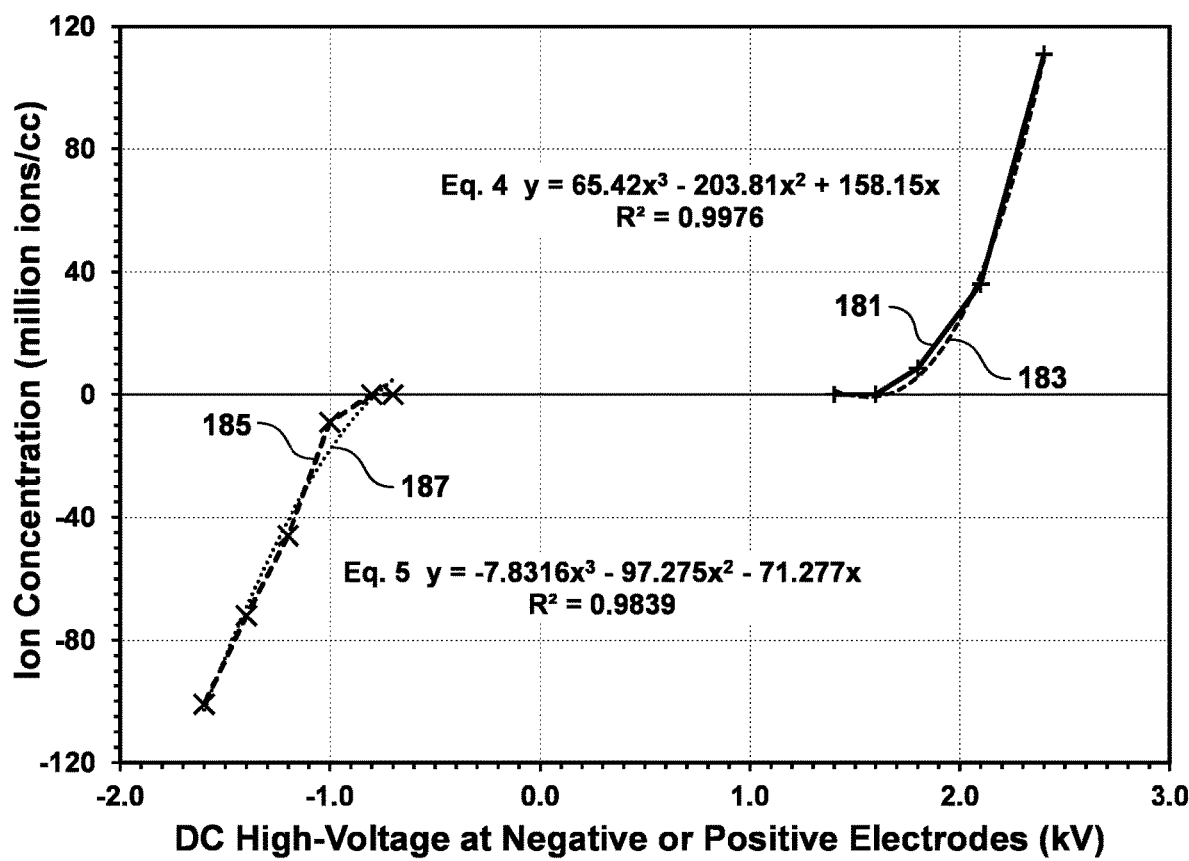
FIG. 18 provides the mathematical relationship between the at least one feedback signal comprising a DC high-voltage positive signal or a DC high-voltage negative signal and a positive or negative ion concentration.

FIG. 18 provides laboratory test data and a first curve 181 showing a positive ion concentration in million ions per cubic centimeter (ions/cc) versus a DC high-voltage positive signal in kilovolts (kV). FIG. 18 also provides a second curve 185 showing a negative ion concentration in million ions/cc curve versus a DC high-voltage negative signal (kV). Ion concentrations are measured using an accurate ion counter Model AIC2 manufactured by Alpha Labs Inc. (https://www.alphalabinc.com/product/aic2/). FIG. 18 provides a third curve 183 showing a first equation (Eq. 4) based on a regression equation of the laboratory test data of the positive ion concentration in million ions/cc versus the DC high-voltage positive signal (kV). Eq. 4 may be used to calculate the positive ion concentration (million ions/cc) based on accurate measurements of the DC high-voltage positive signal (kV). The method calculates and reports the positive-ion concentration based on a first equation (Eq. 4) where an independent variable is the positive DC high-voltage signal.

$$y=65.42X^3-203.81X^2+158.15x \qquad \text{Eq. 4}$$

Where, y=positive ion concentration (million ions/cc), and x=DC high-voltage positive signal (kV).

FIG. 18 provides a fourth curve 187 showing a second equation (Eq. 5) based on a regression equation of the laboratory test data of the negative ion concentration in million ions/cc versus the DC high-voltage negative signal (kV). Eq. 5 may be used to calculate the negative ion concentration (million ions/cc) based on accurate measurements of the DC high-voltage negative signal (kV). The method calculates and reports the negative-ion concentration based on a second equation where the independent variable is the negative DC high-voltage signal.

$$y=-7.8316x^3-97.275x^2-71.277x \qquad \text{Eq. 5}$$

Where, y=negative ion concentration (million ions/cc), and x=DC high-voltage negative signal (kV).

Figure 19:
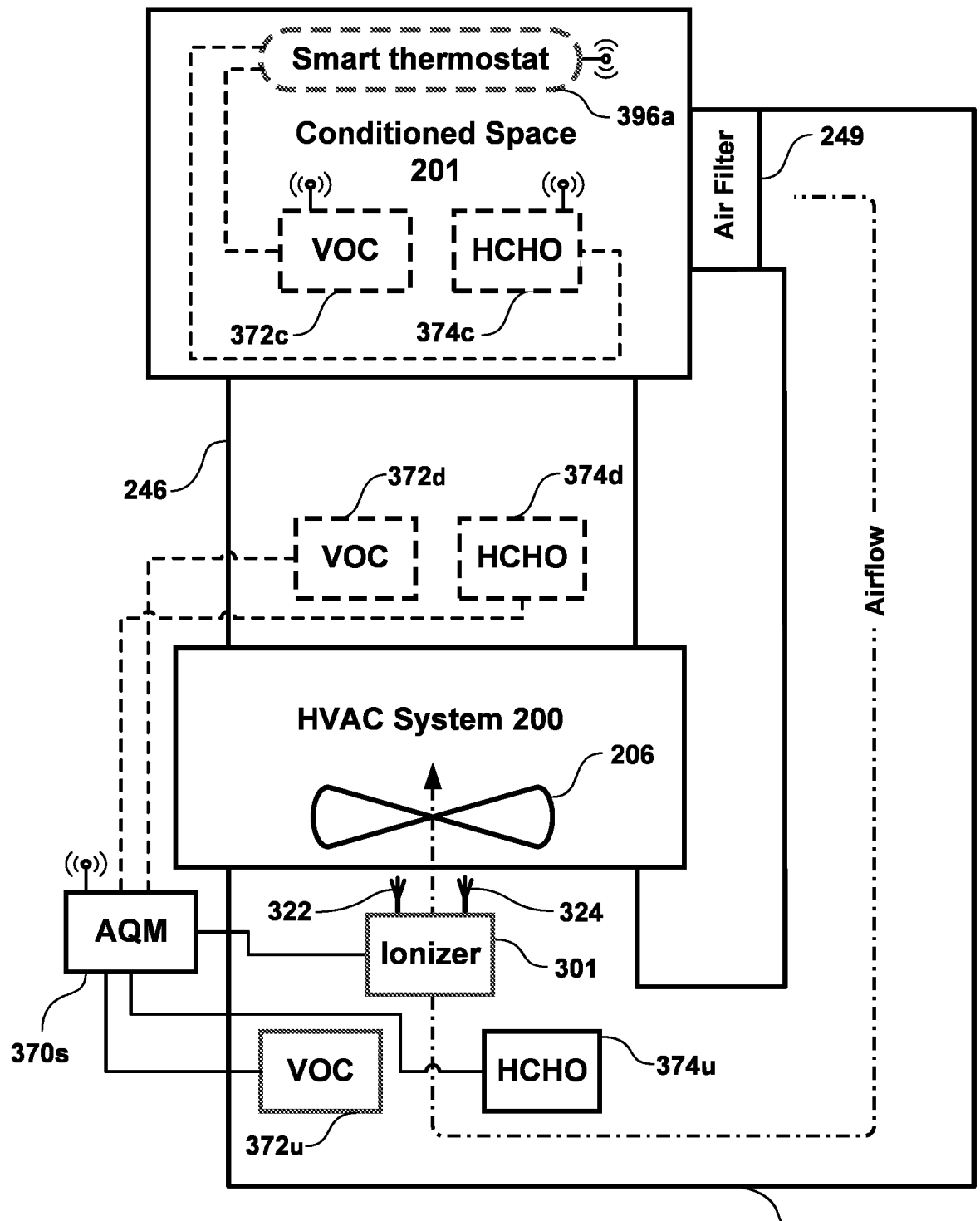
FIG. 19 shows at least one air filter and sensors to measure VOCs, formaldehyde, and PM 2.5 (not shown) installed upstream of the ionizer and similar sensors installed downstream of the ionizer and in the conditioned space.

FIG. 19 shows the ionizer 301 with positive-ion electrode 322 and/or a negative-ion electrode 324 installed at the inlet of the fan 206 of the HVAC system 200 (both electrodes could be negative). The VOC sensor 372u and the formaldehyde sensor or the HCHO sensor 374u and the at least one air filter 249 are installed upstream of the bipolar ionizer. The at least one sensor or the at least one air filter may be installed with the bipolar ionizer where the at least one sensor is installed upstream or downstream of the bipolar ionizer and the at least one air filter is installed upstream of the bipolar ionizer. A Minimum Efficiency Reporting Value (MERV) rated air filter with the manganese oxide catalyst may be comprised of at least one catalyst selected from the group consisting of: a manganese sulfate or MnSO4 catalyst, a sodium permanganate or NaMnO4 catalyst, and a cryptomelane potassium manganese oxide mineral or K(Mn4+, Mn2+)8O16 catalyst. The AQM 370s is connected to these sensors and the VOC sensor 372d and HCHO sensor 374d which are installed downstream of the bipolar ionizer. The AQM 370s is also shown with wireless communication or bluetooth to communicate with the smart thermostat or other device such as a mobile phone smart home device, smart watch, computer, network, or automobile. The supply duct 246 connects the HVAC system 200 to the conditioned space

201 and the return duct 248 connects the conditioned space 201 to the HVAC system 200.

FIG. 19 shows a smart thermostat 396*a* controlling the HVAC system 200 and connected to the VOC sensor 372*c* and the HCHO sensor 374*c*. Wireless or bluetooth communication antennas are shown on the smart thermostat 396*a*, the VOC sensor 372*c*, and the HCHO sensor 374*c*. A PM 2.5 sensor (not shown) may also be installed with each set of sensors. FIG. 19 shows the at least one sensor or the at least one air filter may be installed upstream or downstream of the ionizer and the at least one air filter may be installed upstream of the ionizer. The at least one air filter is selected from the group consisting of: the MERV rated air filter with activated carbon, a High Efficiency Particulate Air (HEPA) filter, or the MERV rated air filter with manganese oxide catalysts comprising at least one catalyst selected from the group consisting of: a manganese sulfate or MnSO4 catalyst, a sodium permanganate or NaMnO4 catalyst, and a cryptomelane potassium manganese oxide mineral or K(Mn4+,Mn2+)8O16 catalyst. The air filter may comprise manganese oxide catalysts to remove formaldehyde through catalytic oxidation to the avoid producing concentrations of smaller, potentially oxidized daughter VOCs such as HCHO. FIG. 19 shows the AQM 370*s* and/or smart thermostat 396*a* monitoring the DC high-voltage electrode signals, ion concentrations, VOCs, HCHO, or PM 2.5 concentrations and controlling the ionizer 301, the HVAC system 200, or the fan 206 to improve indoor air quality, thermal comfort, and energy efficiency. The ionizer 301 and the at least one air filter 249 reduce or eliminate pollutants (VOCs, HCHO, and PM 2.5) and pathogens (viruses, bacteria, fungi, mold).

Known bipolar ionizers may produce high ozone concentrations greater than the 24-hour Time Weighted Average (TWA) of 0.05 parts per million by volume (ppmv) per regulations established by the California Air Resources Board (CARB) for indoor air cleaning devices (AB 2276) or the United States (US) Food and Drug Administration (FDA). High ozone concentrations create an unresolved problem regarding human health. Field tests indicate that some bipolar ionizers may produce nearly zero bipolar ionization when installed with opposing magnetic fields from rare earth magnets used to attach bipolar ionizers to sheet metal surfaces of HVAC ducts or fan housings. Research studies indicate bipolar ionizers may enhance concentrations of smaller, potentially oxidized daughter VOCs such as HCHO (Zeng et al 2021).

The present invention comprises a feedback control to provide consistent DC high-voltage output over a range of 20 to 30 VAC electric signal inputs to provide consistent ion concentrations to deactivate pathogens and produce zero or 0.0 ppmv ozone concentrations over a 24-hour TWA. The present invention also comprises sensors to monitor VOCs and/or HCHO in the airflow being treated by the ionizer. If the monitored VOC and/or HCHO concentrations are greater than a threshold level, then the present invention de-energizes or reduces the positive DC high-voltage output and/or the negative DC high-voltage output to stop generating the ion concentration or reduce the ion concentration energy to avoid producing or enhancing concentrations of smaller, potentially oxidized daughter VOCs or HCHO.

The ionizer comprises: (1) at least one input terminal for at least one electrical signal input to energize the bipolar ionizer; (2) a signal conditioning element to process the at least one electrical signal input and provide an analog or a digital signal; (3) a step-up transformer to receive the analog or the digital signal from the signal conditioning element and provide a step-up transformer output voltage; (4) a negative voltage multiplier to receive the step-up transformer output voltage and provide a negative high-voltage output to a negative-ion electrode to generate a negative-ion concentration; and (5) a positive voltage multiplier to receive the step-up transformer output voltage and provide a positive high-voltage output to a positive-ion electrode to generate a positive-ion concentration, wherein: the positive voltage multiplier and the negative voltage multiplier provide a high-voltage output ratio less than 80 percent, and the high-voltage output ratio is equal to a minimum of an absolute value of a negative high-voltage output and a positive high-voltage output, divided by a maximum of the absolute value of the negative high-voltage output and the positive high-voltage output.

The signal conditioning element comprises at least one electrical component selected from the group consisting of: (1) a wire to conduct only one electrical signal input and provide the excitation signal to the step-up transformer, (2) at least one optically isolated triac to conduct the at least one electrical signal input and provide the excitation signal to the step-up transformer, (3) at least one relay to conduct the at least one electrical signal input and provide the excitation signal to the step-up transformer, (4) two diodes and a capacitor to conduct the at least one electrical signal input to a resistor and a Zener diode, a microprocessor, and a first FET to provide the excitation signal to the step-up transformer, and (5) two diodes and a capacitor to conduct the at least one electrical signal input to two resistors, a capacitor, a Zener diode, an oscillator, and the first FET to provide the excitation signal to the step-up transformer.

The signal conditioning element further includes: (1) at least one Resistor Divider Network (RDN) to reduce the positive high-voltage output or the negative high-voltage output to produce at least one high-impedance voltage signal; and (2) at least one active element selected from the group consisting of: an Operational Amplifier (Op Amp), a second FET, and a feedback comparator, wherein the at least one active element converts the at least one high-impedance voltage signal to at least one feedback signal, wherein the at least one feedback signal is used by a microprocessor to vary a frequency and a duty cycle of a digital signal 421 to a first FET 314 to control the excitation signal 422 for the step-up transformer and modulate the frequency and the duty cycle of the step-up transformer output voltage to maintain the high-voltage output ratio less than 80 percent and generate the bipolar ion concentration ratio greater than 80 percent to minimize an ozone concentration over a range of electrical signal inputs described above. The at least one active element maintains a consistent negative DC high-voltage output to a negative-ion electrode to generate a negative-ion concentration and a consistent positive DC high-voltage output to a positive-ion electrode to generate a positive-ion concentration.

The at least one feedback signal is a low-voltage feedback signal or a comparator feedback signal. The at least one input terminal further may be at least two input terminals to allow the at least one electrical signal input to energize the bipolar ionizer wherein the at least one electrical signal input is selected from at least two electrical signal inputs. The at least one electrical signal input is used to energize the bipolar ionizer to avoid operating the bipolar ionizer continuously which wastes energy and causes dust to accumulate on the negative-ion electrode or the positive-ion electrode when a fan is off which reduces the negative-ion concentration or the positive-ion concentration. The positive voltage multiplier provides at least one more multiplier stage than the negative voltage multiplier or the negative voltage multiplier provides at least one more multiplier stage than the positive voltage multiplier to provide the high-voltage output ratio less than 80 percent and the bipolar ion concentration ratio greater than 80 percent. The bipolar ionizer may include a Light Emitting Diode (LED) or a wireless communication module and antenna to provide status information or fault alarm messages.

The ionizer control converts at least one Direct Current (DC) high-voltage signal to at least one feedback signal where the at least one DC high-voltage signal is selected from the group consisting of: a NDHS on a negative-ion electrode generating a negative-ion concentration, and a PDHS on a positive-ion electrode generating a positive-ion concentration. The method also comprises monitoring the at least one feedback signal corresponding to the at least one DC high-voltage signal and comparing the at least one feedback signal to a first specification to determine whether the at least one feedback signal is within the first specification. The method varies a frequency and a duty cycle of a digital signal to control an excitation signal for a step-up transformer and modulates the frequency and the duty cycle of a step-up transformer output voltage to consistently maintain the at least one feedback signal within the first specification and maintain the at least one DC high-voltage signal within a second specification to generate a consistent ion concentration over a range of electrical signal inputs.

The at least one feedback signal is a low-voltage feedback signal or a comparator feedback signal and the first specification for the at least one feedback signal is selected from the group consisting of: a Negative Low-voltage Feedback Signal (NLFS) first specification is +1.7V+/−0.4V to +2.5V+/−0.6V where the NLFS is inverted to a positive signal and is approximately one one-thousandth of the NDHS, a Positive Low-voltage Feedback Signal (PLFS) first specification is +1.7V+/−0.4V to +2.5V+/−0.6V where the PLFS is approximately one one-thousandth of the PDHS, a Negative Comparator Feedback Signal (NCFS) first specification is between 0 and 1 where the NCFS is 1 when the NDHS is less than the second specification and the NCFS is 0 when the NDHS is greater than the second specification, and a Positive Comparator Feedback Signal (PCFS) first specification is between 0 and a 1where the PCFS is 1 when the PDHS is greater than the second specification and the PCFS is 0 when the PDHS is less than the second specification. The second specification for the at least one DC high-voltage signal is selected from the group consisting of: the NDHS second specification is −2.5 kV+/−0.6 kV to −1.7 kV+/−0.4 kV, and the PDHS second specification is +1.7 kV+/−0.4 kV to +2.5 kV+/−0.6 kV. The range of electrical signal inputs is selected from the group consisting of: 20 to 30 VAC, 110 to 130 VAC, 210 to 250 VAC, 208 to 280 VAC, 2 to 15 VDC, and 20 to 30 VDC.

The ionizer control method comprises monitoring and processing the at least one feedback signal and calculating and reporting at least one parameter selected from the group consisting of: a positive DC high-voltage signal, the positive-ion concentration based on a first equation with the positive feedback signal as a first independent variable, a negative DC high-voltage signal, and the negative-ion concentration based on a second equation with the negative feedback signal as a second independent variable. Reporting may include providing data to a software application on a computer, a mobile phone, a watch, or other electronic communications technology regarding the at least one parameter. The ionizer control method may also comprise reporting at least one message selected from the group consisting of: a continuous LED signal, a discontinuous or flashing LED signal, an analog electrical signal, a digital electrical signal, a text message, an email message, a graphical display, an audio communication, a voice mail message, or a wireless communication method. The wireless communication may use a cellular system, a WIFI (wireless fidelity), a Bluetooth (short-range wireless using UHF radio waves in the ISM bands, from 2.402 GHz to 2.480 GHz), a Low-Power Wide-Area Network (LPWAN with data rates from 0.3 kbit/s to 50 kbit/s per channel), or an ultra-low power Long-range Radio (LoRa) or LoRA Wide Area Network (LoRaWAN) communication protocol. Reporting may include at least one ionizer fault selected from the group consisting of: an electrical short on the negative-ion electrode, a power supply voltage input fault beyond a specified range, a power supply or transformer failure, and an electronic component failure.

The ionizer control method may comprise monitoring a Volatile Organic Compound (VOC) concentration or a formaldehyde (HCHO) concentration in an airflow serving the ionizer, and de-energizing or adjusting the DC high-voltage signal and the ion concentration when the VOC concentration is greater than or equal to a first threshold or the HCHO concentration is greater than or equal to a second threshold. The first threshold for the VOC concentration is 0.4 parts per million by volume (ppmv), and the second threshold for the HCHO concentration is 0.1 ppmv.

The method may provide soft power cycling comprising rebooting a microprocessor controlling the ionizer wherein the rebooting occurs for several minutes after a fan providing airflow to the ionizer has been operating continuously for more than several hours wherein the rebooting is performed to enhance an ionizer lifetime and clear accumulated errors in the microprocessor memory to improve performance of the microprocessor and the ionizer.

The method may include installing at least one air filter upstream of the ionizer where the at least one air filter is selected from the group consisting of: a Minimum Efficiency Reporting Value (MERV) rated air filter with activated carbon, a High Efficiency Particulate Air (HEPA) filter, or the MERV rated air filter with a manganese oxide catalyst wherein the MERV rated air filter with the manganese oxide catalyst is comprised of at least one catalyst selected from the group consisting of: a manganese sulfate or $MnSO_4$ catalyst, a sodium permanganate or $NaMnO_4$ catalyst, and a cryptomelane potassium manganese oxide mineral or $K(Mn^{4+},Mn^{2+})_8O_{16}$ catalyst.

While the invention herein disclosed has been described by means of specific embodiments and applications thereof, numerous modifications and variations could be made thereto by those skilled in the art without departing from the scope of the invention set forth in the claims.

The invention claimed is:

1. A method for controlling an ionizer, the method comprising:
    converting at least one Direct Current (DC) high-voltage signal to at least one feedback signal wherein the at least one DC high-voltage signal is selected from the group consisting of:
        a Negative DC High-voltage Signal (NDHS) on a negative-ion electrode generating a negative-ion concentration, and
        a Positive DC High-voltage Signal (PDHS) on a positive-ion electrode generating a positive-ion concentration;
    monitoring the at least one feedback signal corresponding to the at least one DC high-voltage signal and comparing the at least one feedback signal to a first specification to determine whether the at least one feedback signal is within the first specification; and varying a frequency and a duty cycle of a digital signal to control an excitation signal for a step-up transformer and modulating the frequency and the duty cycle of a step-up transformer output voltage to consistently maintain the at least one feedback signal within the first specification and maintain the at least one DC high-voltage signal within a second specification to generate a consistent ion concentration over a range of electrical signal inputs.

2. The method of claim 1, wherein the at least one feedback signal is a low-voltage feedback signal or a comparator feedback signal and the first specification for the at least one feedback signal is selected from the group consisting of:
- a Negative Low-voltage Feedback Signal (NLFS) first specification is +1.7V+/−0.4V to +2.5V+/−0.6V where the NLFS is inverted to a positive signal,
- a Positive Low-voltage Feedback Signal (PLFS) first specification is +1.7V+/−0.4V to +2.5V+/−0.6V,
- a Negative Comparator Feedback Signal (NCFS) first specification is between 0 and 1 where the NCFS is 1 when the NDHS is less than the second specification and the NCFS is 0 when the NDHS is greater than the second specification, and
- a Positive Comparator Feedback Signal (PCFS) first specification is between 0 and a 1 where the PCFS is 1 when the PDHS is greater than the second specification and the PCFS is 0 when the PDHS is less than the second specification.

3. The method of claim 1, wherein the second specification for the at least one DC high-voltage signal is selected from the group consisting of:
- the NDHS second specification is −2.5 kV+/−0.6 kV to −1.7 kV+/−0.4 kV, and
- the PDHS second specification is +1.7 kV+/−0.4 kV to +2.5 kV+/−0.6 kV.

4. The method of claim 1, wherein the range of electrical signal inputs is selected from the group consisting of: 20 to 30 Volts Alternating Current (VAC), 110 to 130 VAC, 210 to 250 VAC, 208 to 280 VAC, 2 to 15 Volts Direct Current (VDC), and 20 to 30 VDC.

5. The method of claim 1, further including processing the at least one feedback signal and calculating and reporting at least one parameter selected from the group consisting of:
- the positive DC high-voltage signal,
- the positive-ion concentration based on a first equation with the positive feedback signal as a first independent variable,
- The negative DC high-voltage signal, and
- the negative-ion concentration based on a second equation with the negative feedback signal as a second independent variable;
wherein the reporting includes providing at least one message selected from the group consisting of: a continuous LED signal, a discontinuous or flashing LED signal, an analog electrical signal, a digital electrical signal, a text message, an email message, a graphical display, an audio communication, a voice mail message or a wireless communication method.

6. The method of claim 1, further including:
monitoring at least one ionizer fault selected from the group consisting of:
- an electrical short on the negative-ion electrode or the positive-ion electrode,
- a power supply voltage input fault beyond a specified range,
- a power supply or transformer failure, and
- an electronic component failure; and
reporting the at least one ionizer fault by providing at least one message selected from the group consisting of: a discontinuous or flashing LED signal, an analog electrical signal, a digital electrical signal, a text message, an email message, a graphical display, an audio communication, a voice mail message, or a wireless communication method.

7. The method of claim 1, further including processing the at least one feedback signal and calculating and reporting at least one parameter selected from the group consisting of:
- the positive DC high-voltage signal,
- the positive-ion concentration based on a first equation with the positive feedback signal as a first independent variable,
- the negative DC high-voltage signal, and
- the negative-ion concentration based on a second equation with the negative feedback signal as a second independent variable;
wherein the reporting includes providing data to a software application on a computer, a mobile phone, a watch, or other electronic communications technology regarding the at least one parameter.

8. The method of claim 1, further including:
monitoring a Volatile Organic Compound (VOC) concentration or a formaldehyde (HCHO) concentration in an airflow serving the ionizer; and
de-energizing or adjusting the DC high-voltage signal and the ion concentration when the VOC concentration is greater than or equal to a first threshold of 0.4 parts per million by volume (ppmv) or the HCHO concentration is greater than or equal to a second threshold of 0.1 ppmv.

9. The method of claim 1, further including:
rebooting a microprocessor controlling the ionizer wherein the rebooting occurs for several minutes after a fan providing airflow to the ionizer has been operating continuously for more than several hours wherein the rebooting is performed to enhance an ionizer lifetime and clear accumulated errors in a microprocessor memory to improve performance of the microprocessor and the ionizer.

10. A method for controlling an ionizer, the method comprising:
converting a Negative DC High-voltage Signal (NDHS) to at least one feedback signal when the NDHS is operating on a negative-ion electrode and generating a negative-ion concentration;
monitoring the at least one feedback signal corresponding to the NDHS and comparing the at least one feedback signal to a first specification to determine whether the at least one feedback signal is within the first specification; and
varying a frequency and a duty cycle of a digital signal to control an excitation signal for a step-up transformer and modulating the frequency and the duty cycle of a step-up transformer output voltage to consistently maintain the at least one feedback signal within the first specification and maintain the NDHS within a second specification to generate a consistent ion concentration over a range of electrical signal inputs.

11. The method of claim 10, wherein the first specification for the at least one feedback signal is selected from the group consisting of:

a Negative Low-voltage Feedback Signal (NLFS) first specification is +1.7V+/−0.4V to +2.5V+/−0.6V where the NLFS is inverted to a positive signal, and a Negative Comparator Feedback Signal (NCFS) first specification is between 0 and 1 where the NCFS is 1 when the NDHS is less than the second specification and the NCFS is 0 when the NDHS is greater than the second specification.

12. The method of claim 10, wherein the second specification for the NDHS is −2.5 kV +/−0.6 kV to −1.7 kV+/−0.4 kV.

13. The method of claim 10, wherein the range of electrical signal inputs is selected from the group consisting of: 20 to 30 Volts Alternating Current (VAC), 110 to 130 VAC, 210 to 250 VAC, 208 to 280 VAC, 2 to 15 Volts Direct Current (VDC), and 20 to 30 VDC.

14. The method of claim 10, further including processing the feedback signal and calculating and reporting at least one parameter selected from the group consisting of:
the negative DC high-voltage signal, and
the negative-ion concentration based on a second equation with the negative feedback signal as a second independent variable;
wherein the reporting includes providing at least one message selected from the group consisting of: a continuous LED signal, a discontinuous or flashing LED signal, a text message, an email message, a graphical display, an audio communication, a voice mail message, or a wireless communication method.

15. The method of claim 10, further including:
monitoring at least one ionizer fault selected from the group consisting of:
an electrical short on the negative-ion electrode,
a power supply voltage input fault beyond a specified range,
a power supply or transformer failure, and
an electronic component failure; and
reporting the at least one ionizer fault by providing at least one message selected from the group consisting of: a discontinuous or flashing LED signal, a text message, an email message, a graphical display, an audio communication, a voice mail message, or a wireless communication method.

16. The method of claim 10, further including processing the feedback signal and calculating and reporting at least one parameter selected from the group consisting of:
the negative DC high-voltage signal, and
the negative-ion concentration based on a second equation with the negative feedback signal as a second independent variable;
wherein the reporting includes providing data to a software application on a computer, a mobile phone, a watch, or other electronic communications technology regarding the at least one parameter.

17. The method of claim 10, further including:
monitoring a Volatile Organic Compound (VOC) concentration or a formaldehyde (HCHO) concentration in an airflow serving the ionizer; and
de-energizing or adjusting the DC high-voltage signal and the ion concentration when the VOC concentration is greater than or equal to a first threshold of 0.4 parts per million by volume (ppmv) or the HCHO concentration is greater than or equal to a second threshold of 0.1 ppmv.

18. The method of claim 10, further including:
rebooting a microprocessor controlling the ionizer wherein the rebooting occurs for several minutes after a fan providing airflow to the ionizer has been operating continuously for more than several hours wherein the rebooting is performed to enhance an ionizer lifetime and clear accumulated errors in a microprocessor memory to improve performance of the microprocessor and the ionizer.

19. A method for controlling an ionizer, the method comprising:
converting at least one Direct Current (DC) high-voltage signal to at least one feedback signal wherein the at least one DC high-voltage signal is selected from the group consisting of:
a Negative DC High-voltage Signal (NDHS) on a negative-ion electrode generating a negative-ion concentration, and
a Positive DC High-voltage Signal (PDHS) on a positive-ion electrode generating a positive-ion concentration;
monitoring the at least one feedback signal corresponding to the at least one DC high-voltage signal and comparing the at least one feedback signal to a first specification to determine whether the at least one feedback signal is within the first specification;
varying a frequency and a duty cycle of a digital signal to control an excitation signal for a step-up transformer and modulating the frequency and the duty cycle of a step-up transformer output voltage to consistently maintain the at least one feedback signal within the first specification and maintain the at least one DC high-voltage signal within a second specification to generate a consistent ion concentration over a range of electrical signal inputs; and
monitoring a Volatile Organic Compound (VOC) concentration or a formaldehyde (HCHO) concentration in an airflow serving the ionizer and de-energizing or adjusting the at least one DC high-voltage signal when the VOC concentration is greater than or equal to a first threshold or the HCHO concentration is greater than or equal to a second threshold.

20. The method of claim 19, wherein the at least one feedback signal is a low-voltage feedback signal or a comparator feedback signal and the first specification for the at least one feedback signal is selected from the group consisting of:
a Negative Low-voltage Feedback Signal (NLFS) first specification is +1.7V+/−0.4V to +2.5V+/−0.6V where the NLFS is inverted to a positive signal,
a Positive Low-voltage Feedback Signal (PLFS) first specification is +1.7V+/−0.4V to +2.5V+/−0.6V,
a Negative Comparator Feedback Signal (NCFS) first specification is between 0 and 1 where the NCFS is 1 when the NDHS is less than the second specification and the NCFS is 0 when the NDHS is greater than the second specification, and
a Positive Comparator Feedback Signal (PCFS) first specification is between 0 and a 1 where the PCFS is 1 when the PDHS is greater than the second specification and the PCFS is 0 when the PDHS is less than the second specification.

21. The method of claim 19, wherein the second specification for the at least one DC high-voltage signal is selected from the group consisting of:
the NDHS second specification is −2.5 kV+/−0.6 kV to −1.7 kV+/−0.4 kV, and
the PDHS second specification is +1.7 kV+/−0.4 kV to +2.5 kV+/−0.6 kV.

22. The method of claim 19, where the first threshold for the VOC concentration is 0.4 parts per million by volume (ppmv) and the second threshold for the HCHO concentration is 0.1 ppmv.

\* \* \* \* \*